(12) United States Patent
Port et al.

(10) Patent No.: US 8,986,650 B2
(45) Date of Patent: Mar. 24, 2015

(54) COMPLEX FOLATE-NOTA-GA68

(75) Inventors: Marc Port, Deuil la Barre (FR); Claire Corot, Lyons (FR); Thierry Gautheret, Bois-le-Roi (FR)

(73) Assignee: Guerbet, Villepinte (FR)

( * ) Notice: Subject to any disclaimer, the term of this patent is extended or adjusted under 35 U.S.C. 154(b) by 459 days.

(21) Appl. No.: 13/205,352

(22) Filed: Aug. 8, 2011

(65) Prior Publication Data

US 2012/0064003 A1  Mar. 15, 2012

Related U.S. Application Data

(63) Continuation-in-part of application No. 12/083,269, filed as application No. PCT/EP2006/067211 on Oct. 9, 2006.

(30) Foreign Application Priority Data

Oct. 7, 2005 (FR) ..................... 05 10289
Apr. 5, 2006 (FR) ..................... 06 02975

(51) Int. Cl.
| | |
|---|---|
| A61K 51/00 | (2006.01) |
| A61M 36/14 | (2006.01) |
| A61K 51/04 | (2006.01) |
| C07D 209/48 | (2006.01) |
| C07D 239/95 | (2006.01) |
| C07D 295/15 | (2006.01) |
| C07D 487/04 | (2006.01) |

(52) U.S. Cl.
CPC .......... *A61K 51/0459* (2013.01); *C07D 209/48* (2013.01); *C07D 239/95* (2013.01); *C07D 295/15* (2013.01); *C07D 487/04* (2013.01)
USPC ........... 424/1.69; 424/1.11; 424/1.65; 534/15

(58) Field of Classification Search
CPC ....... A61K 51/00; A61K 51/02; A61K 51/04; A61K 51/041; A61K 51/0482; A61K 51/06; A61K 51/065; A61K 2123/00; A61K 2121/00; A61K 47/48107; A61K 47/30; A61K 49/04; A61K 49/00; A61K 49/002; A61K 49/004; A61K 49/12; C07D 239/95; C07D 487/04; C07D 209/48; C07D 295/15
USPC ............. 424/1.11, 1.65, 1.73, 1.81, 9.1, 1.69; 534/7, 10–16; 514/1, 1.1; 540/465, 474
See application file for complete search history.

(56) References Cited

U.S. PATENT DOCUMENTS

| | | | |
|---|---|---|---|
| 5,334,371 A | 8/1994 | Gries et al. | |
| 5,403,572 A | 4/1995 | Gries et al. | |
| 5,707,605 A | 1/1998 | Meade et al. | |
| 5,712,389 A | 1/1998 | Meyer et al. | |
| 5,919,432 A | 7/1999 | Meyer et al. | |
| 6,071,490 A | 6/2000 | Griffiths et al. | |
| 6,261,535 B1 | 7/2001 | Thorpe et al. | |
| 6,264,914 B1 | 7/2001 | Klaveness et al. | |
| 6,372,194 B1 | 4/2002 | Akaike et al. | |
| 6,391,280 B1 | 5/2002 | Hiatt et al. | |
| 6,410,695 B1 | 6/2002 | Sinn et al. | |
| 6,440,956 B1 | 8/2002 | Port | |
| 6,489,333 B2 | 12/2002 | Pitts et al. | |
| 6,491,893 B1 | 12/2002 | Babich | |
| 6,511,648 B2 | 1/2003 | Harris et al. | |
| 6,524,554 B1 | 2/2003 | Edwards et al. | |
| 6,534,038 B2 | 3/2003 | Liu | |
| 6,537,520 B1 | 3/2003 | Rajopadhye et al. | |
| 6,827,927 B1 | 12/2004 | Rousseaux et al. | |
| 2002/0106325 A1 | 8/2002 | Carpenter | |
| 2002/0128553 A1 | 9/2002 | Mishani et al. | |
| 2003/0082106 A1 | 5/2003 | Nivorozhkin et al. | |
| 2003/0152513 A1 | 8/2003 | Blankenberg et al. | |
| 2004/0210041 A1 | 10/2004 | Arbogast et al. | |
| 2005/0048000 A1 | 3/2005 | Gervais et al. | |
| 2005/0191238 A1 | 9/2005 | Casebier et al. | |
| 2005/0201943 A1 | 9/2005 | Nivorozhkin et al. | |
| 2006/0233704 A1 | 10/2006 | Maecke et al. | |

(Continued)

FOREIGN PATENT DOCUMENTS

| | | |
|---|---|---|
| EP | 0 352 218 A2 | 1/1990 |
| EP | 0 425 212 A2 | 5/1991 |
| EP | 0 438 206 A1 | 7/1991 |

(Continued)

OTHER PUBLICATIONS

J. Schuhmacher et al., "GRP Receptor—Targeted PET of a Rat Pancreas Carcinoma Xenograft in Nude Mice with a 68Ga-Labeled Bombesin(6-14)Analog", The Journal of Nuclear Medicine, 2005, Vol: 46 No. 4, pp. 691-699

J.P. Andre, "1,4,7-Triazacyclononane-1-succinic acid-4,7-diacetic acid (NODASA): a new bifunctional chelator for radio gallium-labelling of biomolecules", Chemical Communications, 1998, No. 12, pp. 1301-1302.

(Continued)

*Primary Examiner* — D L Jones

(74) *Attorney, Agent, or Firm* — Birch, Stewart, Kolasch & Birch, LLP

(57) ABSTRACT

The present invention concerns a Ga68 complex of formula FOLATE-(LINKER)i-NOTA-Ga$^{68}$ in which:

1) FOLATE is a folate compound or a derivative thereof capable of targeting a folate receptor, 2) NOTA is a chelate capable of complexing Ga68 having a NOTA scaffold or derivatives thereof 3) LINKER is a chemical group linking FOLATE and NOTA 4) i is an integer chosen between 0 and 1 wherein NOTA is complexing Ga68.

9 Claims, 1 Drawing Sheet

(1 of 1 Drawing Sheet(s) Filed in Color)

(56) References Cited

U.S. PATENT DOCUMENTS

| | | | |
|---|---|---|---|
| 2007/0098643 A1 | 5/2007 | Nachman et al. | |
| 2007/0258905 A1 | 11/2007 | Aime et al. | |

FOREIGN PATENT DOCUMENTS

| | | | |
|---|---|---|---|
| EP | 0 661 279 A1 | 7/1995 | |
| EP | 1 121 377 | 4/2000 | |
| JP | 10-501528 A | 2/1998 | |
| JP | 2004-509152 A | 3/2004 | |
| WO | WO 93/19787 A | 10/1993 | |
| WO | 94/00489 | 1/1994 | |
| WO | WO 94/04485 A | 3/1994 | |
| WO | WO 94/05269 | 3/1994 | |
| WO | WO 95-32741 A1 | 12/1995 | |
| WO | WO 96/36367 | 11/1996 | |
| WO | WO 98/39288 A | 9/1998 | |
| WO | WO 99/40947 | 8/1999 | |
| WO | WO 99/54317 | 10/1999 | |
| WO | WO 00/61195 | 10/2000 | |
| WO | WO 00/71526 A1 | 11/2000 | |
| WO | WO 01/00637 A1 | 1/2001 | |
| WO | WO 01/09188 A1 | 2/2001 | |
| WO | WO 01/10450 A1 | 2/2001 | |
| WO | WO 01/52900 A2 | 7/2001 | |
| WO | WO 01/60416 A2 | 8/2001 | |
| WO | WO 01/77102 A1 | 10/2001 | |
| WO | WO 01/77122 A1 | 10/2001 | |
| WO | WO 01/77145 A2 | 10/2001 | |
| WO | WO 01/97850 A2 | 12/2001 | |
| WO | WO 01/97861 A2 | 12/2001 | |
| WO | WO 01/98294 A2 | 12/2001 | |
| WO | WO 02/26776 A2 | 4/2002 | |
| WO | WO 02/28441 A2 | 4/2002 | |
| WO | WO 02/32292 A2 | 4/2002 | |
| WO | WO 02/38546 A1 | 5/2002 | |
| WO | WO 02/40060 A | 5/2002 | |
| WO | WO 0244156 A2 | 6/2002 | |
| WO | WO 02/053192 A1 | 7/2002 | |
| WO | WO 02/054088 A2 | 7/2002 | |
| WO | WO 02/056670 A2 | 7/2002 | |
| WO | WO 02/059110 A1 | 8/2002 | |
| WO | WO 02/062810 A2 | 8/2002 | |
| WO | WO 02/066512 A1 | 8/2002 | |
| WO | WO 02/081497 A2 | 10/2002 | |
| WO | WO 02/085908 A1 | 10/2002 | |
| WO | WO 02/094873 A2 | 11/2002 | |
| WO | WO 03/006059 A1 | 1/2003 | |
| WO | WO 03/008300 A1 | 1/2003 | |
| WO | WO 03/011115 A2 | 2/2003 | |
| WO | WO 03/013346 A | 2/2003 | |
| WO | WO 03/014145 A2 | 2/2003 | |
| WO | WO 03/018640 A2 | 3/2003 | |
| WO | WO 03/020701 A2 | 3/2003 | |
| WO | WO 03/059397 A | 7/2003 | |
| WO | WO 03/074523 A2 | 9/2003 | |
| WO | WO 03/077727 A2 | 9/2003 | |
| WO | WO 03/078569 A2 | 9/2003 | |
| WO | WO 03/086475 A1 | 10/2003 | |
| WO | WO 03/086476 A1 | 10/2003 | |
| WO | WO 2004/058275 A2 | 7/2004 | |
| WO | WO 2004/069365 A1 | 8/2004 | |
| WO | WO 2004/089425 A1 | 10/2004 | |
| WO | WO 2004/089517 A | 10/2004 | |
| WO | WO 2004/112839 A2 | 12/2004 | |
| WO | WO 2004/112840 A2 | 12/2004 | |
| WO | WO 2005/002293 A2 | 1/2005 | |
| WO | WO 2005/009393 A2 | 2/2005 | |
| WO | WO 2005/012335 A1 | 2/2005 | |
| WO | WO 2005/019247 A2 | 3/2005 | |
| WO | WO 2005/023314 A2 | 3/2005 | |
| WO | WO 2005/042033 A1 | 5/2005 | |
| WO | WO 2005/044312 A1 | 5/2005 | |
| WO | WO 2005/044313 A2 | 5/2005 | |
| WO | WO 2005/046563 A2 | 5/2005 | |
| WO | WO 2005/049095 A2 | 6/2005 | |
| WO | WO 2005/049096 A2 | 6/2005 | |
| WO | WO 2005/079886 A2 | 9/2005 | |
| WO | WO 2005/082425 A1 | 9/2005 | |
| WO | WO 2005/082889 A1 | 9/2005 | |
| WO | WO 2005/084168 A2 | 9/2005 | |
| WO | WO 2006/002873 A2 | 1/2006 | |
| WO | WO 2006/071754 A2 | 7/2006 | |
| WO | WO 2006/090232 A | 8/2006 | |
| WO | WO 2006/095234 A2 | 9/2006 | |
| WO | WO 2006/100305 A | 9/2006 | |
| WO | WO 2007/042504 A2 | 4/2007 | |
| WO | WO 2010/092114 A1 | 8/2010 | |

OTHER PUBLICATIONS

K.P. Eisenwiener et al., "NODAGATOC, a New Chelator-Coupled Somatostatin Analogue Labeled with 67/68Ga and [111In] for SPECT, PET, and Targeted Therapeutic Applications of Somatostatin Receptor (hsst2) Expressing Tumors", Bioconjuoate Chemistry, 2002, vol. 13, No. 3, pp. 530-541.

Froidevaux, S. et al. "A Gallium-Labeled DOTA-alpha-Melanocyte-Stimulating Hormone Analog for PET Imaging of Melanoma Metastases" The Journal of Nuclear Medicine, vol. 45, No. 1, Jan. 2004, pp. 116-123. XP 002364150.

Henze M et al., "PET imaging of Somatostatin Receptors Using [68GA]DOTA-D-Phe1-Octreotide: First Results in Patients with Meningiomas" Journal of Nuclear Medicine, vol. 42, No. 7, Jul. 2001, pp. 1053-1056.

Hoffend J et al., "Gallium-68-DOTA-albumin as a PET blood-pool marker: experimental evaluation in vivo" Nuclear Medicine and Biology, vol. 32, 2005, pp. 287-292.

International Search Report, dated Jul. 12, 2007 in PCT/EP2006/067211.

Moerlein, S.M. et al., "A Gallium-68 Labeled Chemotactic Peptide Analogue for Imaging Focal Sites of Bacterial Infection by PET." Symposium Abstracts, Paper 19, pp. 426-427. XP008010914. (1992).

Nakamoto, Yuji et al. "Effects of Nonionic Intravenous Contrast Agents at PET/CT Imaging: Phantom and Canine Studies" Radiology, vol. 227, No. 3, Jun. 2003 pp. 817-824. XP002413062.

Velikyan I et al., "Preparation and Evaluation of 68Ga-DOTA-hEFG for Visualization of EGFR Expression in Malignant Tumors" Journal of Nuclear Medicine, Society of Nuclear Medicine, vol. 46, No. 11, Nov. 2005, pp. 1881-1888.

Favoni et al., "The Role of Polypeptide Growth Factors in Human Carcinomas: New Targets for a Novel Pharmacological Approach", Pharmacological Reviews, vol. 52, No. 2 (2000) pp. 179-206.

Kling et al., "Design and Synthesis of 1,5- and 2,5-Substituted Tetrahydrobenzazepinones as Novel Potent and Selective Integrin $\alpha v\beta 3$ Antagonists", Bioorganic & Medicinal Chemistry, vol. 11 (2003) pp. 1319-1341.

Krause, "Liver-Specific X-Ray Contrast Agents", Topics in Current Chemistry, vol. 222 (1992) pp. 173-199.

Liu et al., "Fundamentals of Receptor-Based Diagnostic Metalloradiopharmaceuticals", Topics in Current Chemistry, vol. 222 (1992) pp. 259-278.

Luyt et al., "A Trithiolate Tripodal Bifunctional Ligand for the Radiolabeling of Peptides with Gallium (III)", Bioconjugate Chem., vol. 13 (2002) pp. 1140-1145.

Mathias et al., "Indium-111-DTPA-Folate as a Potential Folate-Receptor-Targeted Radiopharmaceutical", J. of Nuclear Medicine, vol. 39 (1996) pp. 1579-1585.

Morikawa et al., "Treatment of Focal Cerebral Ischemia with Synthetic Oligopeptide Corresponding to Lectin Domain of Selectin", Stroke, vol. 27 (1996) pp. 951-956.

Siegel et al., "Evaluation of 111In-DTPA-Folate as a Receptor-Targeted Diagnostic Agent for Ovarian Cancer: Initial Clinical Results", J. of Nuclear Medicine, vol. 44, No. 5 (2003) pp. 700-707.

Zheng et al., "Multimodal Contast Agent for Combined Computed Tomography and Magnetic Resonance Imaging Applications", Investigative Raiology, vol. 41, No. 3 (2006) pp. 339-348.

COMPLEX FOLATE-NOTA-GA68

CROSS REFERENCE TO RELATED APPLICATIONS

This application is a Continuation-in-Part of U.S. patent application Ser. No. 12/083,269, filed on Apr. 7, 2008 and for which priority is claimed under 35 U.S.C. §120. Application Ser. No. 12/083,269 is the National Phase of PCT International Application No. PCT/EP2006/067211, filed on Oct. 9, 2006 under 35 U.S.C. §371, which also claims priority of Application Nos. 0510289 and 0602975, filed in France on Oct. 7, 2005 and Apr. 5, 2006, respectively. All of the above-identified applications are hereby expressly incorporated by reference into the present application.

Folates are important vitamins for physiological cell division and replication, since they are involved as coenzymes in the synthesis of a number of amino acids as well as nucleic acids. Cellular folate transport can be mediated by the folate receptor (FR), a membrane-anchored protein which binds physiologic folates with high affinity in the low nanomolar level. FRs are only scarcely expressed in most normal tissues, while elevated expression has frequently been observed in a wide variety of human cancers (e.g. breast, cervical, colorectal, renal, and nasopharyngeal), including >90% of ovarian and endometrial carcinomas. Thus, FR has been used as a target for selective delivery of drugs to these tumors, such as radiopharmaceuticals, MRI contrast agents, chemotherapeutic agents, antisense oligonucleotides, protein toxins and liposomes with entrapped drugs. Once folate conjugates are bound to FR they are transported into the cell through receptor-mediated endocytosis.

Several compounds and studies in the scientific literature deal with folate compounds attached to chelating moieties for use in the imaging diagnostic field.

Most of the folate-based radiopharmaceuticals have been developed for SPECT imaging (photon emission, with use of radionuclides emitting energy of the order of 100 to 200 keV, in particular), labeled with 99mTc or 111In. Among these radioconjugates 111In-DTPA-folate (DTPA: diethylenetriaminepentaacetic acid), developed by Green, Low et al., has been evaluated in patients suffering from ovarian cancer, in a phase I/II study [Siegel et al, J Nucl Med, 2003, 44:700-7]. 111In-DTPA-folate exhibited rapid target-tissue uptake and non target-tissue clearance, which gives the possibility of image acquisition at early time points after injection, while differentiation between benign and malignant masses was possible in patients with suspected new disease. Despite the encouraging results of the study more attention was paid to the development of 99mTc-labeled folate conjugates mainly because of the short half-life of 99mTc (t½=6 h), its availability (generator produced) and cost effectiveness, parameters important for routine clinical application.

SPECT Compounds have however several limits SPECT gives a poorer spatial resolution than PET imaging and can involve visualization of the patient 2 to 3 days after the administration of the product due to the lifetime of certain isotopes such as In111, which is a big disadvantage for the clinical practice.

Folate compounds for PET with F18 radionuclides have also been studied.

PET imaging (emission of positrons giving rise to an emission of photons detected by a PET scanner) using the F18 radionuclide is particularly used for the metabolic monitoring of tumor zones using FDG (fluorodeoxyglucose).

Nowadays Positron Emission Tomography (PET) is becoming a dominating method in molecular imaging, since it combines the potential to quantify the tracer uptake within lesions with a relatively high resolution and a remarkably high sensitivity of up to 10-12 M.

A major drawback of the use of the common isotopes such as F18 in PET is the need for a cyclotron which produces the isotope, in general in the vicinity of the site where the product is administered to the patient, given the lifetime of the isotopes, which poses considerable problems in terms of cost and logistics.

Folate compounds for PET with Ga68 have been also studied.

The lifetime of Ga68 is 68 minutes, which makes its use in clinical PET possible, but, as for F18 (the half-life of which is 121 minutes), it requires a short time for preparing the product incorporating the Ga68, preferably less than approximately 40 minutes and much preferably less than 15 minutes.

In combination with computerized tomography (CT), providing anatomic information, hybrid instruments were developed that make the new technique PET/CT even more powerful. Among the β+-emitters used for PET imaging 68Ga [t½=67.71 min, β+=740 keV (89%)] deserves special attention. Its availability from long-lived 68Ge/68Ga-generators, cost effectiveness, rendering 68Ga radiopharmacy possible in each hospital, well established coordination chemistry of Ga3+ that allows developing agents resistant to in vivo transchelation of 68Ga3+ and its suitable imaging properties make it attractive for clinical application.

Folate conjugates for gallium complexation have been mentioned using deferoxamine DF as a chelator. The 66/67/68Ga-DF-folate conjugates showed good pharmacokinetics but also exhibited partial hepatobiliary clearance which is considered a limitation in cases of accurately imaging of regio-abdominal locations in humans, such as ovarian carcinoma. In order to overcome this obstacle the same group replaced DF with DTPA, which is ideal for labeling with 111In [Mathias et al, Nucl Med, 1998, 39:1579-85], but not with 67/68Ga. However DTPA is not a good complexing agent of Ga68. Another well known chelate DOTA can be used, but it needs for Ga68 complexation a heating or microwave treatment, which is not optimal for folate ligands that are vitamins sensitive to such treatment.

Folate compounds are also described in the patent literature.

WO9636367 describes compounds comprising a chelate and a folate derivative. EP 825878 describes folate compounds in general terms for MRI or nuclear medicine. These compounds are used for MRI when they are coupled to a lanthanide such as Gadolinium, or for nuclear medicine SPECT modality when they are coupled to a radionuclide such as Technecium or Indium adapted for SPECT irradiation This document does not specifically describe the compounds for PET labeled with Ga68 that are claimed in the present application. In particular it describes a deferoxamine chelate and it is mentioned that the structure of the chelate is not critical provided that it has a requisite affinity for the radionuclide cation. It is reminded that deferoxamine is a long linear chelate that is completely different from the macrocyclic chelates of the compounds claimed.

WO2006071754 relates specifically to folate compounds for imaging of inflammation. Radionuclides dedicated to PET are described in general terms and this document focuses on compounds using F18 isotopes. These compounds do not comprise a chelating group since the radioisotope F18 is grafted directly to a chemical group notably aromatic cycle of the folate molecule.

As a whole, despite the abundant prior art there is still need for a very efficient folate compound usable for diagnostic imaging. The applicant has now found specific compounds comprising a NOTA type chelate coupled to folate derivatives:

As regards to known folate compounds labeled with F18 for PET imaging, these new compounds are very advantageous since they do not need a cyclotron.

As regards to folate compounds comprising a chelate that may be complexed by Ga68 for PET imaging, compounds having a NOTA derivative chelate are very satisfying for Ga68 complexation. In particular they do not need to be heated for complexation with Ga68. Thus the "cold" (meaning not radioactive) compound comprising the chelate and the folate derivative can be prepared in advance, and the complexation of Ga68 can be made at room temperature in an automatic apparatus to produce the radiolabeled compound to be injected to the patient.

As regards to known folate compounds labeled with radionuclides for SPECT imaging, the compounds of the applicant exhibit outstanding properties for clinical imaging. PET Ga68 is of particular interest over SPECT for folate associated pathologies, in particular due to the following criteria:

spatial resolution of PET is much higher, which allows to detect precisely pathologic (in particular tumor) areas of only about 2-4 mm, instead of 10-15 mm, and thus early detection and treatment sensibility of PET is much higher (detection by PET-CT is about 1-10% whereas it is only 0.1% for SPECT-CT), which allows to use a much lower dose of product and thus to avoid uncontrolled pharmaceutical action of the diagnostic product, and an eventual saturation effect of the diagnostic agent, quantification of PET is much better which is a key point in molecular imaging, being very advantageous for the monitoring of therapeutic treatment.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Figure 1:
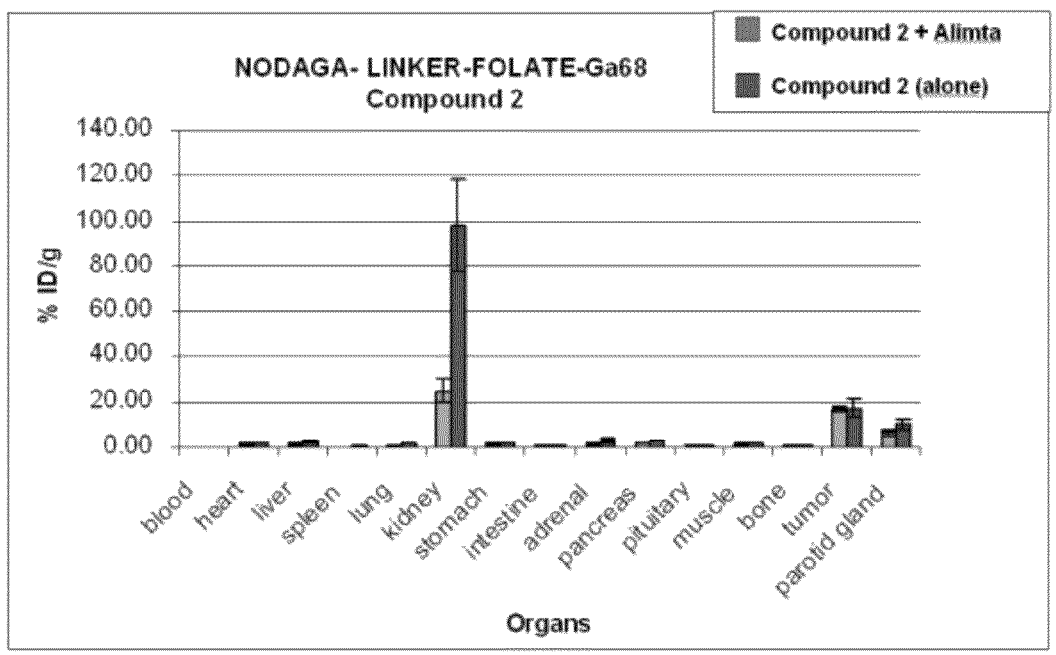
FIG. 1 shows the biodistribution results with NODAGA-LINKER-FOLATE-Ga68.

According to one embodiment, the invention relates to a Ga68 complex of formula FOLATE-(LINKER)i-NOTA-$Ga^{68}$ in which:

1) FOLATE is a folate compound or a derivative thereof capable of targeting a folate receptor, 2) NOTA is a chelate capable of complexing Ga68 having a NOTA scaffold or derivatives thereof such as NETA, TACN-HP and NODA-GA, Advantageously NOTA has the following formula

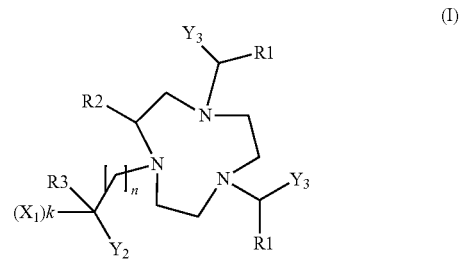

(I)

wherein $Y_3$ represents a group capable of coordinating Ga68, advantageously chosen in the group constituting of *—(C=O)—$Y_4$ and

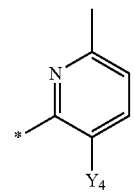

in which * represents the biding site to the rest of the NOTA molecule and $Y_4$ is a group capable of coordinating Ga68, advantageously $Y_4$ is chosen in the group constituting of —O$^-$, —OH, —OPO$_3^-$ or —NHR in which R represents a $C_1$-$C_6$ alkyl group, advantageously $Y_4$ is a —OH group. Advantageously $Y_3$ represents a group *—(C=O)—$Y_4$ in which $Y_4$ is as defined above, more advantageously in which $Y_4$ represents a —OH group.

R1 represents a hydrogen atom or a phenyl group substituted by the group NCS, advantageously a hydrogen atom;

R2 represents a hydrogen atom, a —(CH$_2$)j-COOH group a-(CH$_2$)j-NH$_2$ group, a-(CH$_2$)j-CO—* group or a-(CH$_2$)j-NH* group in which j is an integer from 1 to 10, advantageously 1 or 2, still more advantageously 1, and * is the linking site to LINKER or FOLATE when i=0.

n is an integer from 0 to 2, advantageously n is 0.

$Y_2$ represents a group capable of coordinating Ga68. Advantageously $Y_2$ is chosen in the group consisting of —(C=O)—$Y_4$,

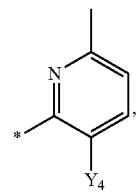

—$Y_4$ and —NR4-CH$_2$—(C=O)—Y4 in which * represents the biding site to the rest of the NOTA molecule, R4 represents a hydrogen atom, a group —CH$_2$COOH, a benzyl group optionally substituted by a —NO$_2$ group or a group —CH$_2$CO* in which * represents the binding site to LINKER or FOLATE when i=0, and Y₄ is as defined above, advantageously Y₂ represents a group *—(C═O)—Y₄, more advantageously Y₄ represents a —OH group.

k=0 or 1, advantageously 1

X₁ is a linking function between the NOTA molecule and the LINKER or FOLATE when i=0. Advantageously X₁ represents a group of formula —(CH₂)ₘ—X₂ in which m is an integer of between 0 and 10, advantageously of between 1 and 5, still more advantageously of 2, and X₂ represents a linking function between the NOTA molecule and LINKER or FOLATE when i=0. Advantageously X₂ is chosen in the group consisting of —CONH—, —COO—, —NHCO—, —NH—, —CO— and —OCO—, more advantageously X₂ represents the group —CONH— or —NH, still more advantageously the group —CONH—.

X1 can also represent a benzyl group substituted by a NO₂ group, a phenyl group substituted by a NCS or a OH group, or a group of the following formula

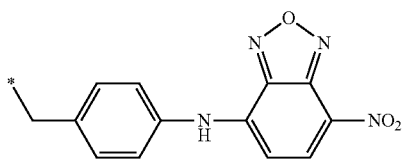

in which * represents the biding site to the rest of the NOTA molecule

R3 represents a hydrogen atom, a benzyl group substituted by a NO₂ group, a phenyl group substituted by a NCS or a OH group, a group of the following formula

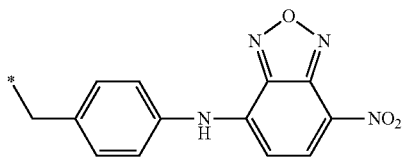 [SMILES: *Cc1ccc(Nc2ccc([N+](=O)[O-])c3nonc23)cc1]

in which * represents the biding site to the rest of the NOTA molecule; or a —(CH₂)₂—COOH group.

Advantageously R3 represents a hydrogen atom

3) LINKER is a chemical group linking FOLATE and NOTA 4) i is an integer chosen between 0 and 1 wherein NOTA is complexing Ga68.

FOLATE has advantageously the following formula:

(A):

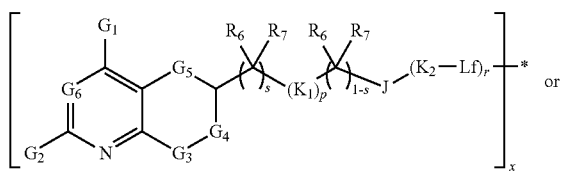

or

-continued (B):

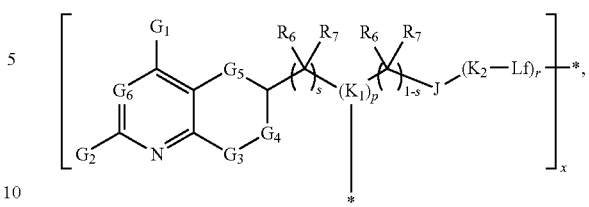

advantageously formula (A), in which:

* represents the site where FOLATE is linked to LINKER or NOTA when i=0;

a) $G_1$ is chosen from the group constituted of: a halogen atom, $R_f2$, $OR_f2$, $SR_f3$ and $NR_f4R_f5$; preferably, $G_1$ is chosen from $NH_2$ and OH, more advantageously $G_1$ is OH;

b) $G_2$ is chosen from the group constituted of: a halogen atom, $R_f2$, $OR_f2$, $SR_f3$ and $NR_f4R_f5$ more advantageously $G_2$ is $NH_2$;

c) G3 represents a divalent group chosen from the group constituted of —($R_f6'$)C═ and —N═, and $G_4$ represents a divalent group chosen from the group constituted of —($R_f6'$)C— and —N—, or $G_3$ represents a divalent group chosen from the group constituted of —($R_f6'$)C— and —N— and $G_4$ represents a divalent group chosen from the group constituted of —($R_f6'$)C═ and —N═, or $G_3$ and $G_4$ represent independently of each other a divalent group chosen independently from the group constituted of —($R_f6'$)C($R_f7'$)— and —N($R_f4'$)— preferably, $G_3$ is —N═ (folic acid) or —CH— (compounds described hereafter: CB3717, raltitrexed, MAI) when the ring comprising $G_3$ is aromatic, and $G_3$ is —NH— or —CH₂— (compounds described hereafter: AG-2034, lometrexol) when the ring comprising G3 is nonaromatic;

preferably, $G_4$ is —CH— or —C(CH₃)— when the ring comprising $G_3$ is aromatic, and —CH₂— or —CH(CH₃)— when the ring comprising $G_3$ is nonaromatic;

Advantageously $G_3$ represents a divalent group chosen from the group constituted of —($R_f6'$)C═ and —N═, and $G_4$ represents a divalent group chosen from the group constituted of —($R_f6'$)C— and —N—. More advantageously $G_4$ represents —($R_f6'$)C—.

More advantageously $G_3$ represents —N═ and $G_4$ represents —($R_f6'$)C— still more advantageously $G_4$ is —CH—.

In another advantageous embodiment $G_3$ represents —($R_f6'$)C═, advantageously —CH═ and $G_4$ represents —($R_f6'$)C— still more advantageously $G_4$ is —CH—.

d) $G_5$ is absent (pemetrexed compound) or chosen from —($R_f6'$)C═, —N═, —($R_f6'$)C($R_f7'$)— and —N($R_f4'$)—; more advantageously $G_5$ is chosen from —($R_f6'$)C═ and —N═;

e) J is a 5- or 6-members aryl or heteroaryl; advantageously J represents a phenyl group f) $G_6$ is N or C (compound described hereafter: 3-deaza-ICI-198,583), advantageously $G_6$ is N;

g) $K_1$ and $K_2$ are chosen independently from the group constituted of —C($Z_f$)—, —C($Z_f$)O—, —OC($Z_f$)—, —N($R_f4''$)—, —C($Z_f$)—N($R_f4$), —N($R_f4''$)—C($Z_f$), —O—C($Z_f$)—N($R_f4''$)—, —N($R_f4$)-C($Z_f$)—O—, N($R_f4$)-C($Z_f$)—N($R_f5''$)—, —O—, —S—, —S(O)—, —S(O)₂—, —N($R_f4$)S(O)₂—, —C($R_f6''$)($R_f7''$)—, —N(C≡CH)—, —N(CH₂—C≡CH)—, C₁-C₁₂ alkyl and C₁-C₁₂ alkoxy; in which Zf is O or S; preferably, $K_1$ is —N($R_f4''$)— or —C(R$_f$6")(R$_f$7")— with R$_f$4", R$_f$6" and R$_f$7" being H; advantageously K$_1$ is —N(R$_f$4")—, more advantageously —NH—;

Advantageously K$_2$ is —C(Z$_f$)—, more advantageously —CO h) R$_f$2, R$_f$3, R$_f$4, R$_f$4', R$_f$4", R$_f$5, R$_f$5", R$_f$6" and R$_f$7" are chosen independently from the group constituted of: H, a halogen atom, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alcynyl, ($C_1$-$C_{12}$ alkoxy)carbonyl, and ($C_1$-$C_{12}$ alkylamino) carbonyl; advantageously R$_f$4", R$_f$6" and R$_f$7" are H, i) R$_f$6' and R$_f$7' are chosen independently from the group constituted of: H, a halogen atom, $C_1$-$C_{12}$ alkyl and $C_1$-$C_{12}$ alkoxy; or R$_f$6' and R$_f$7' together form O═; advantageously R$_f$6' is H;

j)$_R$ $R_6$ and $R_7$ are chosen independently from the group constituted of: H and $C_1$-$C_{12}$ alkyl, advantageously $R_6$ and $R_7$ are both H k) Lf is a divalent linker which includes, where appropriate, a natural amino acid or a natural polyamino acid, such as for example glutamine (Gln), linked to K2 via its alpha-amino group through an amide bond; Advantageously Lf is glutamine l) p, r and s are independently 0 or 1;

m) x is an integer of 1 to 5, advantageously equal to 1.

The formula (A) and (B) includes the tautomer forms thereof, for example of compounds in which $G_1$ is OH, SH or NH.

In this case the tautomer forms of the formula (A) and (B) are as follow:

Tautomer form of (A):

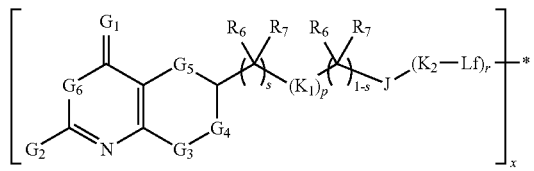

Tautomer form of (B):

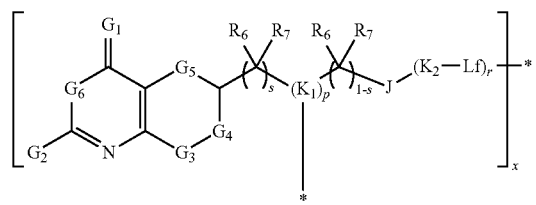

in which $G_2$-$G_5$, $R_6$, $R_7$, $K_1$, $K_2$, Lf, J, s, p, r and x are as defined above, $G_1$ represents O, S or N and $G_6$ represents CH or NH, advantageously $G_1$ represents O, advantageously $G_6$ represents NH.

For the complex of the invention in which at least one of the groups $K_1$, $K_2$, R$_f$1, R$_f$2, R$_f$3, R$_f$4, R$_f$4', R$_f$4", R$_f$5, R$_f$5", R$_f$6, R$_f$7", R$_f$6, R$_f$7, R$_f$6' and R$_f$7' comprises an alkyl, alkoxy, alkylamino, alkanoyl, alkenyl, alkynyl, alkoxycarbonyl or alkylaminocarbonyl group, the group preferably contains 1 to 6 carbon atoms ($C_1$-$C_6$), more preferably 1 to 4 carbon atoms ($C_1$-$C_4$).

Advantageous FOLATE include the following folate derivatives and tautomers thereof a)

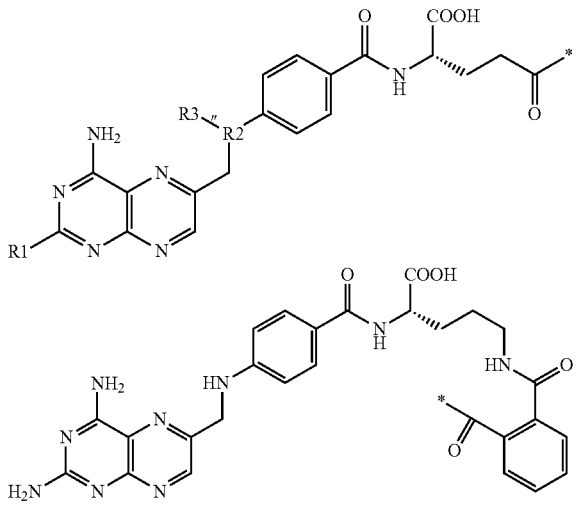

PT523

In which * represents the linking site to LINKER or to NOTA when i=0

|  | R1 | R2 | R3 |  | R1 | R2 | R3 |
|---|---|---|---|---|---|---|---|
| MTX | $NH_2$ | N | $CH_3$ | 2-dAMT | H | N | H |
| 2-dMTX | H | N | $CH_3$ | 2-$CH_3$-AMT | $CH_3$ | N | H |
| 2-$CH_3$-MTX | $CH_3$ | N | $CH_3$ | Edatrexate | $NH_2$ | C | $C_2H_5$ |
| AMT | $NH_2$ | N | H |  |  |  |  | b)

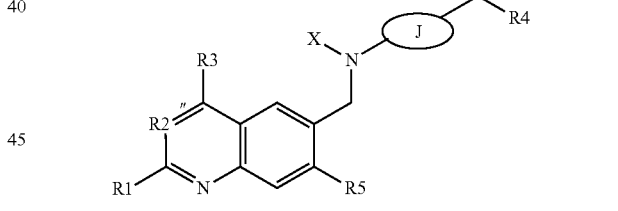

in which J is as defined above

| X = propargyl | R1 | R3 | R4 | R5 |
|---|---|---|---|---|
| CB3717 | $NH_2$ | N | OH | Glu* | H |
| ICI-198,583 | $CH_3$ | N | OH | Glu* | H |
| 3-deaza-ICI-198,583 | $CH_3$ | CH | OH | Glu* | H |
| 4-H-ICI-198,583 | $CH_3$ | N | H | Glu* | H |
| 4-$OCH_3$-ICI-198,583 | $CH_3$ | N | $OCH_3$ | Glu* | H |
| Glu→Val-ICI-198,583 | $CH_3$ | N | OH | Valine* | H |
| Glu→Sub-ICI-198,583 | $CH_3$ | N | OH | Suberate* | H |
| 7-$CH_3$-ICI-198,583 | $CH_3$ | N | OH | Glu* | $CH_3$ |

| X = methyl | R1 | R2 | R4 | R5 |
|---|---|---|---|---|
| Raltitrexed | $CH_3$ | N | OH | Glu* | H |
| 2-$NH_2$-ZD1694 | $NH_2$ | N | OH | Glu* | H |

Glu = glutamic acid
in which * represents the linking site to LINKER or to NOTA when i = 0

Advantageously, FOLATE has the following formula (a1) or (a2)

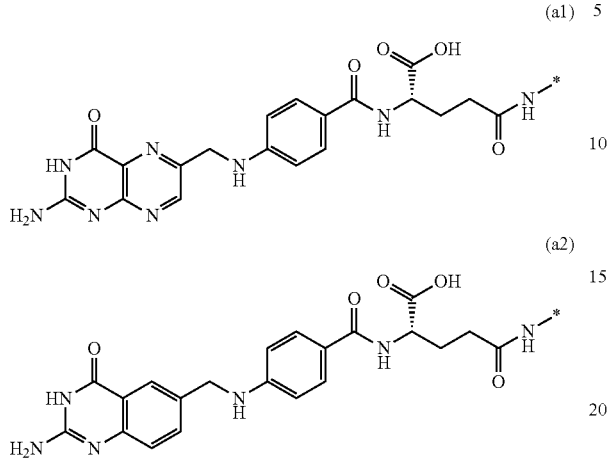

in which * represents the linking site to LINKER or NOTA if i=0 and the tautomer thereof.

FOLATE includes the following derivatives: pteropolyglutamic acid, pteridines capable of targeting the folate receptor (tetrahydropterins, tetrahydrofolates, dihydrofolates in particular).

The folate derivatives also include the following compounds: aminopterin, amethopterin (methotrexate), N-methylfolate, 2-deaminohydroxyfolate; and deaza derivatives thereof such as 1-deazamethopterin or 3-deazamethopterin, and 3',5'-dichloro-4-amino-4-deoxy-N-methylpteroyl-glutamic acid (dichloromethotrexate).

The folate derivatives include the deaza or dideaza compounds. The terms "deaza" and "dideaza" refer to the known derivatives of folic acid, which do not have nitrogen atoms $G_3$, $G_5$, $G_6$. For example, the deaza derivatives include the 1-deaza, 3-deaza, 5-deaza, 8-deaza and 10-deaza derivatives.

LINKER is preferably chosen among the following linkers:

1) amino acids 2) linkers L capable of interacting with at least one FOLATE functional group and at least one NOTA functional group. L includes in particular alkyl chains which are substituted or unsubstituted, saturated or unsaturated, and straight or branched, peptides, polyethylene glycols and polyoxyethylenes. Mention will in particular be made of:

a.1) a single bond,

—$(CH_2)_n$—, —$(CH_2)_nCO$—, —$(CH_2)_nNHCO$—, $(CH_2)_n$CONH—, —$(CH_2)_nCONH$—$(CH_2)_n$— —$(CH_2)_n$phenylNH—, in particular —$(CH_2)_2$phenylNH—, —$(CH_2)_nNH$— in particular —$(CH_2)_3NH$—, —NH$(CH_2)_nNH$— in particular NH$(CH_2)_2NH$ or NH$(CH_2)_3NH$, —$(CH_2)_n$phenyl-, in particular —$(CH_2)_2$phenyl and —NH$(CH_2)_n$— in particular NH$(CH_2)_2$— or NH$(CH_2)_3$—, with n=1-20, advantageously n=2 to 10, $(CH_2CH_2O)_q(CH_2)_rCO$—, $(CH_2CH_2O)_q(CH_2)_rNH$—CO—, —$(CH_2CH_2O)_q(CH_2)_r$—, $(CH_2CH_2O)_q(CH_2)_r$NH— with q=1-10 and r=2-10, —$(CH_2)_n$—CONH-PEG-,

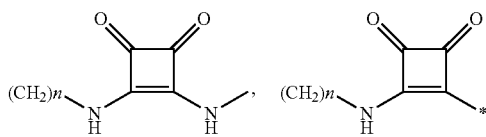

in which * represents the binding site to NOTA,

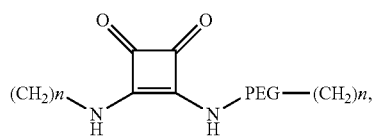

with n=1 to 5 and advantageously n=4 or 5,
CO—$CH_2$—O—$(CH_2)_n$—O—$(CH_2)_p$—O—$CH_2$—CO—, in particular —CO—$CH_2$—O—$(CH_2)_2$—O—$(CH_2)_2$—O—$CH_2$—CO—; —CO—$(CH_2)_n$—$CO_2$—$(CH_2)_p$—OCO—$(CH_2)_q$—CO—, in particular —CO—$(CH_2)_2$—$CO_2$—$(CH_2)_2$—OCO—$(CH_2)_2$—CO—; —CO—CH(OH)—CH(OH)—CO—; —CO—$(CH_2)_n$—CO—; CO—$CH_2$—O—$(CH_2)_p$—O—$(CH_2)_p$—O—$CH_2$—, in particular —CO—$CH_2$—O—$(CH_2)_2$—O—$(CH_2)_2$—O—$CH_2$—; —CO—$(CH_2)_n$—$CO_2$—$(CH_2)_p$—OCO—$(CH_2)_q$—, in particular —CO—$(CH_2)_2$—$CO_2$—$(CH_2)_2$—OCO—$(CH_2)_2$—; —CO—CH(OH)—CH(OH)— and —CO—$(CH_2)_n$—, with n=1-20, p=1-20 and q=1-20;

—NH—$(CH_2)_n$—CO—; —NH—$CH_2$—$(CH_2$—O—$CH_2)_n$—CO_and —NH—$CH_2$—$(CH_2$—O—$CH_2)_n$— with n=1 to 10, linkers denoted A8 to A32 of document WO 2006/095234, pages 104 and 105.

a.2) —P1-l-P2, which may be identical or different, P1 and P2 being chosen from O, S, NH, nothing, $CO_2$, NHCO, CONH, NHCONH, NHCSNH, $SO_2$NH—, $NHSO_2$— and squarate with l=alkyl, alkoxyalkyl, polyalkoxyalkyl (PEG), alkyl interrupted with one or more squarates or with one or more aryls, advantageously phenyls, alkenyl, alkynyl, alkyl which are interrupted with one or more groups chosen from —NH—, —O—, —CO—, —NH(CO)—, —(CO)NH—, —O(CO)—, or —(OC)O—

P1 and P2 are thus groups for coupling LINKER with, on the one hand, NOTA and, on the other hand, FOLATE.

L will, for example, have a molecular weight of between 300 and 2000 g/mol, in particular between 300 and 1000 g/mol.

3) linkers described in U.S. Pat. No. 6,264,914, capable of reacting with amino, hydroxyl, sulfhydryl, carboxyl, carbonyl, carbohydrate, thioether, 2-aminoalcohol, 2-aminothiol, guanidinyl, imidazolyl and phenolic functional groups (of FOLATE and of NOTA); and with the definition summaries of WO 2007/042504.

4) certain linkers described in U.S. Pat. No. 6,537,520 of formula $(Cr_6r_7)_g$—$(W)_h$—$(Cr_{6a}r_{7a})_{g'}$-$(Z)_k$—$(W)_{h'}$—$(Cr_8r_9)_{g''}$-$(W)_{h''}$—$(Cr_{8a}r_{9a})_{g'''}$ with the definitions of this document.

5) certain linkers described in document WO 02/085908, for example a linear or branched chain of a linker, chosen from:

1) CR6'''R7'''-, —(R6''')C═C(R7''')═, —CC—, —C(O)—, —O—, —S—, —$SO_2$—, —N(R3''')-, —(R6''')C═N—, —C(S)—, —P(OO(OR3'''))-, —P(O)—(OR3''')O—, with R'''3 being a group capable of reacting with a nitrogen or an oxygen and with R6''', R7''' and R3''' as defined in WO 02/085908

2) a cyclic region (divalent cycloalkyls, divalent heterocycles)
3) polyalkylenes, polyalkylene glycols.

LINKER is preferably chosen among a single bond,

—(CH$_2$)$_n$—, —(CH$_2$)$_n$CO—, —(CH$_2$)$_n$NHCO—, (CH$_2$)$_n$CONH—, —(CH$_2$)$_n$phenylNH—, in particular —(CH$_2$)$_2$phenylNH—, —(CH$_2$)$_n$NH— in particular —(CH$_2$)$_3$NH—, —NH(CH$_2$)$_n$NH— in particular NH(CH$_2$)$_2$NH or NH(CH$_2$)$_3$NH, —(CH$_2$)$_n$phenyl-, in particular —(CH$_2$)$_2$phenyl and —NH(CH$_2$)$_n$— in particular NH(CH$_2$)$_2$— or NH(CH$_2$)$_3$—, with n=1-20, advantageously n=2 to 10, —(CH$_2$CH$_2$O)$_q$(CH$_2$)$_r$CO—, (CH$_2$CH$_2$O)$_q$(CH$_2$)$_r$NH—CO—, —(CH$_2$CH$_2$O)$_q$(CH$_2$)$_r$—, (CH$_2$CH$_2$O)$_q$(CH$_2$)$_r$NH— with q=1-10 and r=2-10, —(CH$_2$)$_n$—CONH-PEG-,

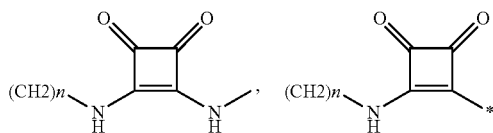

in which * represents the binding site to NOTA,

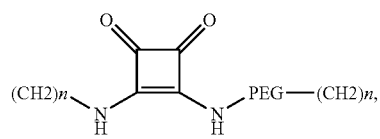

with n=1 to 5 and advantageously n=4 or 5,

CO—CH$_2$—O—(CH$_2$)$_n$—O—(CH$_2$)$_p$—O—CH$_2$—CO—, in particular —CO—CH$_2$—O—(CH$_2$)$_2$—O—(CH$_2$)$_2$—O—CH$_2$—CO—; —CO—(CH$_2$)$_n$—CO$_2$—(CH$_2$)$_p$—OCO—(CH$_2$)$_q$—CO—, in particular —CO—(CH$_2$)$_2$—CO$_2$—(CH$_2$)$_2$—OCO—(CH$_2$)$_2$—CO—; —CO—CH(OH)—CH(OH)—CO—; —CO—(CH$_2$)$_n$—CO—; CO—CH$_2$—O—(CH$_2$)$_n$—O—(CH$_2$)$_p$—O—CH$_2$—, in particular —CO—CH$_2$—O—(CH$_2$)$_2$—O—(CH$_2$)$_2$—O—CH$_2$—; —CO—(CH$_2$)$_n$—CO$_2$—(CH$_2$)$_p$—OCO—(CH$_2$)$_q$—, in particular —CO—(CH$_2$)$_2$—CO$_2$—(CH$_2$)$_2$—OCO—(CH$_2$)$_2$—; —CO—CH(OH)—CH(OH)— and —CO—(CH$_2$)$_n$—, with n=1-20, p=1-20 and q=1-20;

—NH—(CH$_2$)$_n$—CO—; —NH—CH$_2$—(CH$_2$—O—CH$_2$)$_n$—CO— and —NH—CH$_2$—(CH$_2$—O—CH$_2$)$_n$— with n=1 to 10, More advantageously LINKER is chosen among —(CH$_2$)$_n$—, —(CH$_2$)$_n$CO—, —(CH$_2$)$_n$NHCO—, (CH$_2$)$_n$CONH—, —(CH$_2$)$_n$phenylNH—, in particular —(CH$_2$)$_2$phenylNH—, —(CH$_2$)$_n$NH— in particular —(CH$_2$)$_3$NH—, —NH(CH$_2$)$_n$NH— in particular NH(CH$_2$)$_2$NH or NH(CH$_2$)$_3$NH, —(CH$_2$)$_n$phenyl-, in particular —(CH$_2$)$_2$phenyl and —NH(CH$_2$)$_n$—, in particular NH(CH$_2$)$_2$— or NH(CH$_2$)$_3$—, with n=1-20, advantageously n=2 to 10, —(CH$_2$)$_n$—CONH-PEG-,

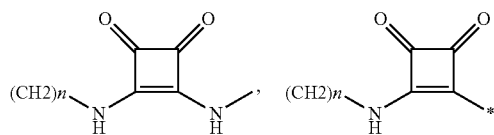

in which * represents the binding site to NOTA,

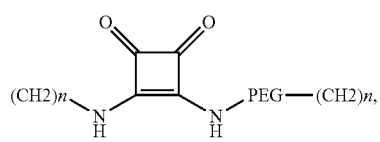

with n=1 to 5 and advantageously n=4 or 5,

Still more advantageously LINKER is chosen among —(CH$_2$)$_n$—, —(CH$_2$)$_n$CO—, —(CH$_2$)$_n$NHCO—, (CH$_2$)$_n$CONH—, —(CH$_2$)$_n$phenylNH—, in particular —(CH$_2$)$_2$phenylNH—, —(CH$_2$)$_n$NH— in particular —(CH$_2$)$_3$NH—, —NH(CH$_2$)$_n$NH— in particular NH(CH$_2$)$_2$NH or NH(CH$_2$)$_3$NH, —(CH$_2$)$_n$phenyl-, in particular —(CH$_2$)$_2$phenyl and —NH(CH$_2$)$_n$— in particular NH(CH$_2$)$_2$— or NH(CH$_2$)$_3$—, with n=1-20, advantageously n=2 to 10.

Even still more advantageously LINKER is —(CH$_2$)$_n$—, with n=1-20, advantageously n=2 to 10, in particular 2. This type of LINKER is particularly advantageous since it is easier to couple the FOLATE and NOTA by using —(CH$_2$)$_n$— and therefore the process of preparation of the compound FOLATE-(LINKER)i-NOTA according to the present invention is easier to carry out.

NOTA is in particular chosen among
1) NOTA

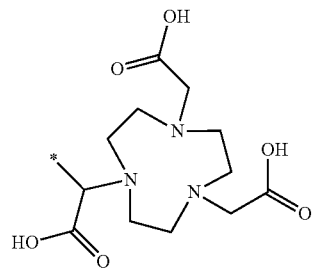 [SMILES: *C(C(=O)O)N1CCN(CC(=O)O)CCN(CC(=O)O)CC1]

wherein * represents the binding site to LINKER of FOLATE when i=0,

2) NODA-GA

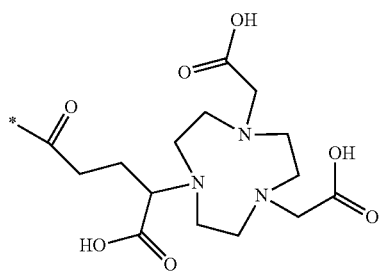 [SMILES: *C(=O)CCC(C(=O)O)N1CCN(CC(=O)O)CCN(CC(=O)O)CC1]

wherein * represents the binding site to LINKER of FOLATE when i=0

3) and any NOTA derivative capable of complexing Ga68, notably one of the following formula wherein * represents the binding site to LINKER of FOLATE when i=0
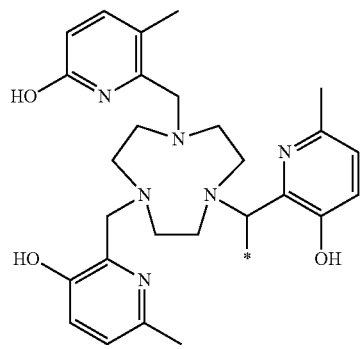
TACN-HP
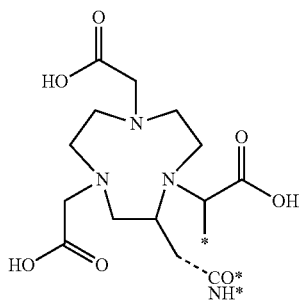
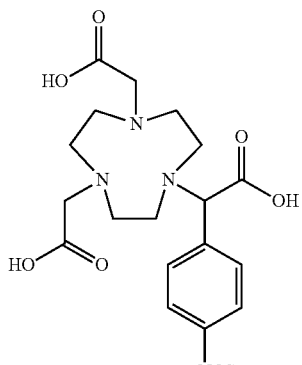
n = 1: NBEA
n = 2: NBPA
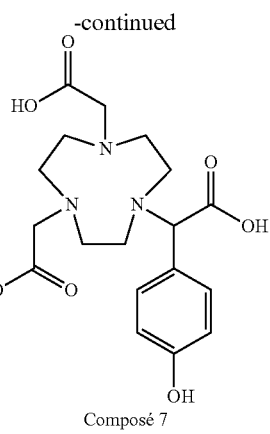
Composé 6
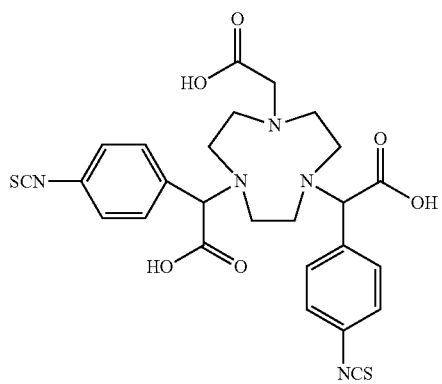
Composé 7
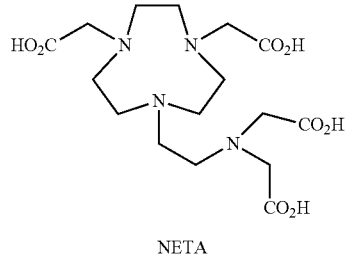
Composé 8
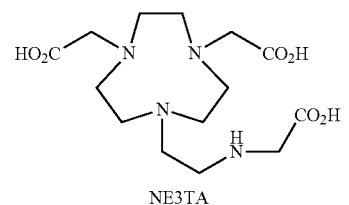
NETA
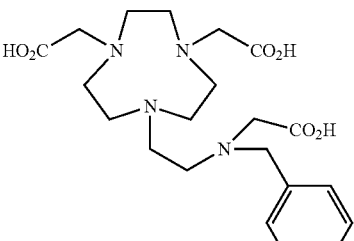
NE3TA
NE3TA-Bn

1) NOTA

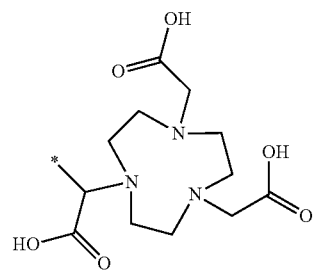 [SMILES: *C(C(=O)O)N1CCN(CC(=O)O)CCN(CC(=O)O)CC1]

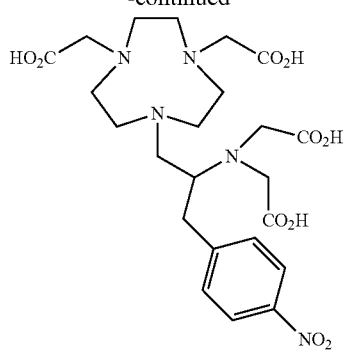
C-NETA wherein * represents the binding site to the —(CH$_2$)$_m$—X$_2$ group, 2) and any NOTA derivative capable of complexing Ga68, notably one of the following formula wherein * represents the binding site to the —(CH$_2$)$_m$—X$_2$ group:

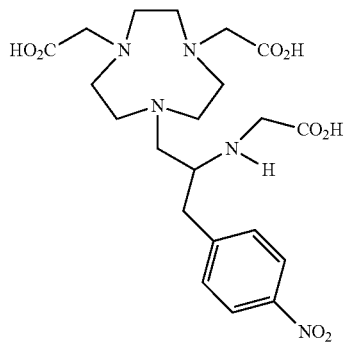
C-NE3TA

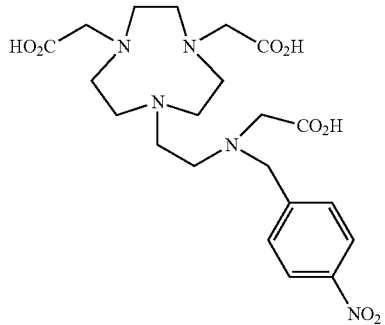
N-NE3TA

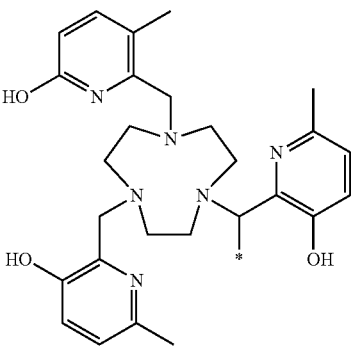
TACN-HP

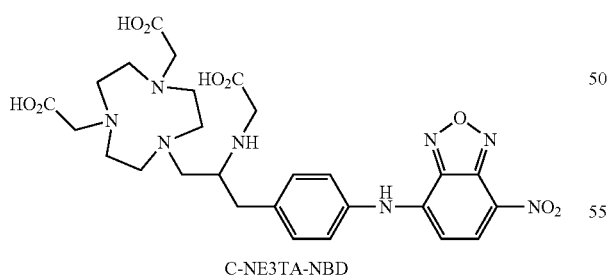
C-NE3TA-NBD

By extension NOTA includes NETA chelates able to complex Ga68 with comparable complexation rate.

NOTA has in particular the following formula:

—X$_2$—(CH$_2$)$_m$—NOTA CHELATE wherein m and X$_2$ are as defined above and NOTA CHELATE is a chelate having a NOTA scaffold well known in the art such as for example:

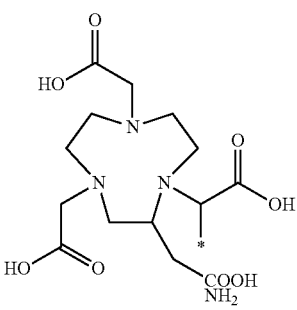

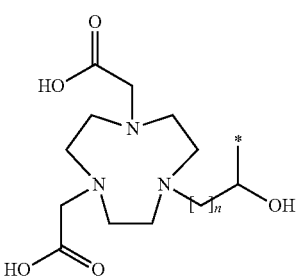
n = 1: NBEA
n = 2: NBPA

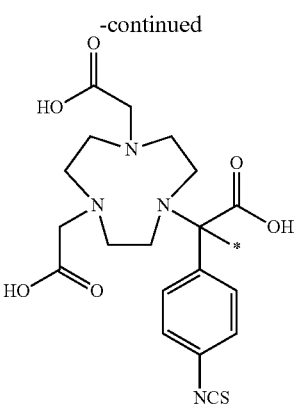

Composé 6

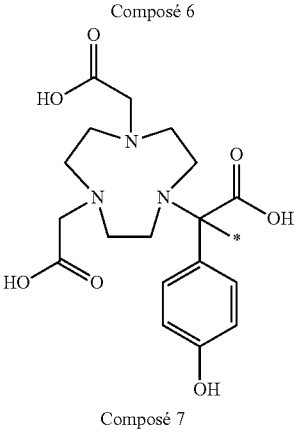

Composé 7

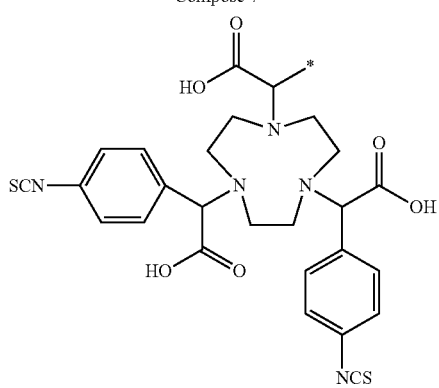

Composé 8

By extension NOTA CHELATE includes NETA chelates able to complex Ga68 with comparable complexation rate.

Preferably NOTA has the following formula (II):

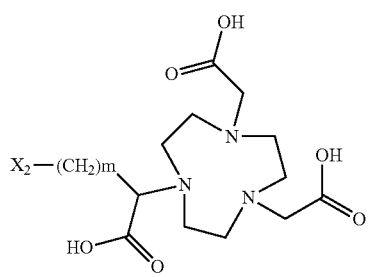

wherein m and $X_2$ are as defined above.

More preferably, when NOTA is complexed with Ga68, NOTA has therefore the following formula III

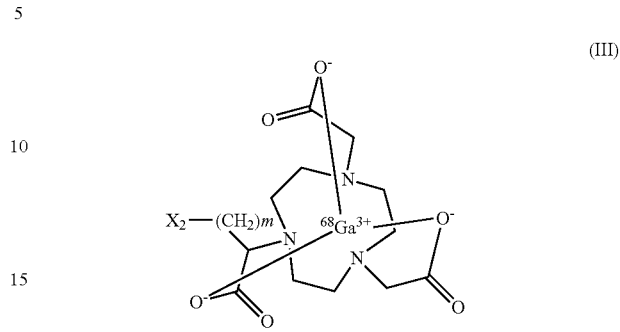

wherein m and $X_2$ are as defined above.

More advantageously, NOTA has the following formula (IV):

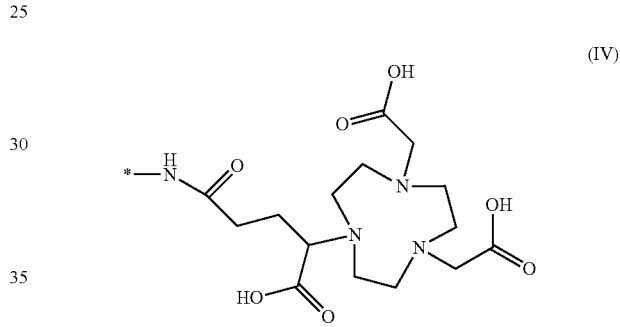

wherein * represents the linking site to LINKER or to NOTA when i=0.

More preferably, when NOTA is complexed with Ga68, NOTA has therefore the following formula V

wherein * represents the linking site to LINKER or to NOTA when i=0.

Preferably LINKER forms with FOLATE a covalent link of the type: —CONH—, —COO—, —NHCO—, —OCO—, —NH—CS—NH—, —C—S—, —S—C—, —N—NH—CO—, —CO—NH—N—, —$CH_2$—NH—, —NH—$CH_2$—, —N—CS—N—, —CO—CH₂—S—, —S—CH₂—CO—, —N—CO—CH₂—S—, —S—CH₂—CO—N—, —N—CO—CH₂—CH₂—S—, —S—CH₂—CH₂—CO—N—, —CH=NH—NH—, —NH—NH=CH—, —CH=N—O—, —O—N=CH— or of the following formula:
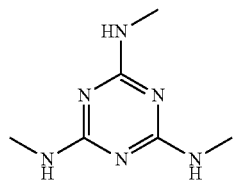
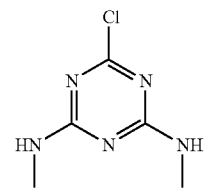
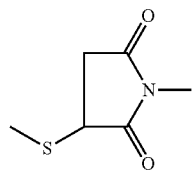
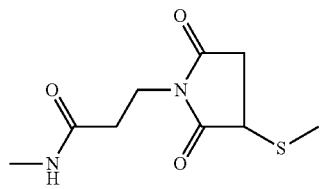
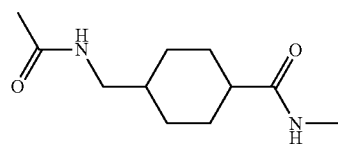
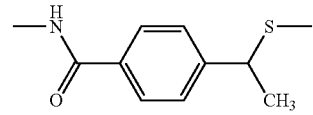
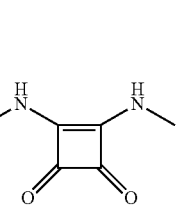
Most preferably a very advantageous compound FOLATE-(LINKER)i-NOTA is chosen between the following formula:
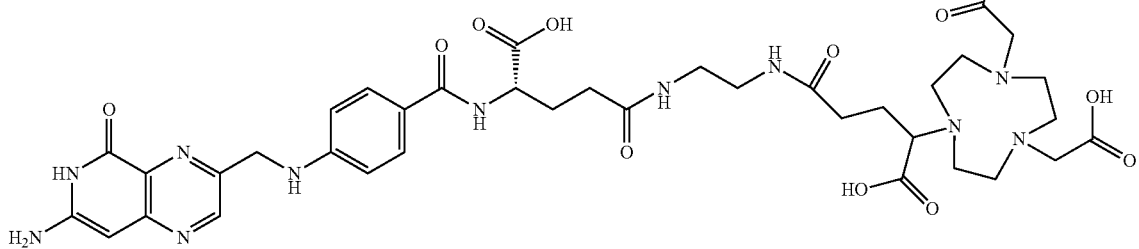
and its dideaza derivative:
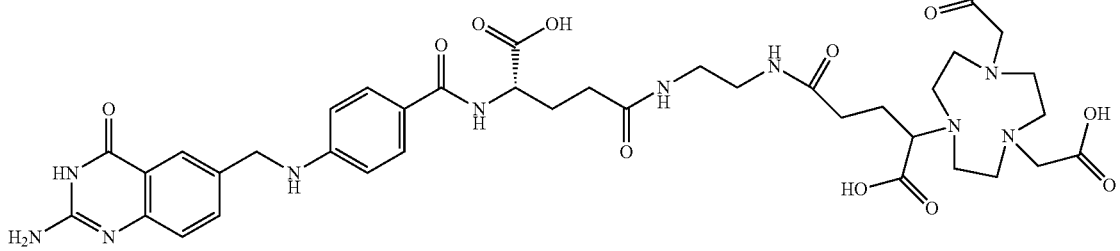

The compound 2' is particularly preferred.

These compounds complexed by Ga68, i.e. very advantageous complex FOLATE-(LINKER)i-NOTA-Ga68, have the following formula:

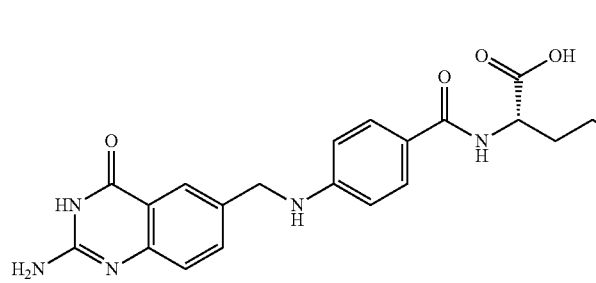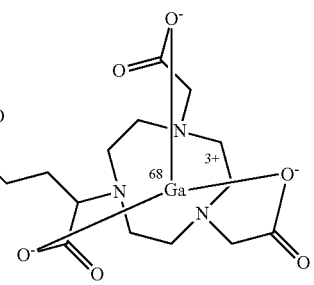

2

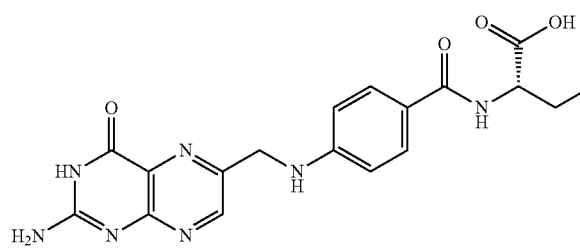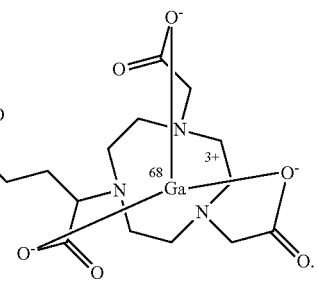

1

Compound 2 is particularly preferred.

The one skilled in the art understands that the LINKER part of the compound can be coupled to the NOTA part of the molecule (NOTA-LINKER prepared and then coupled afterwards to FOLATE) or to the FOLATE part of the molecule (FOLATE-LINKER prepared and then coupled afterwards to NOTA).

The applicant has particularly focused on the use, in PET imaging, of gallium Ga68 since this isotope is produced, not by a cyclotron, but by a generator (germanium Ge68/gallium Ga68), an apparatus which is much less complex and expensive than the cyclotron.

Two preparation processes are possible:
the FOLATE is coupled to NOTA and then the compound formed is complexed with the Ga68 produced by the generator;
the NOTA is complexed with the Ga68 produced by the generator, and then the complex formed is coupled to FOLATE; this embodiment is less advantageous.

Ga68 is obtained by decay of Ge68, the lifetime of which is 270 days. Ge68 generators are based on the use of a matrix which absorbs the Ge68, the Ga68 being eluted.

When the Ga68 leaves the generator, it can be coupled to NOTA, the complex formed being intended to be coupled to FOLATE. According to one variant, NOTA has been coupled to FOLATE beforehand, so that this coupling reaction does not impair the stability of NOTA with gallium. Where appropriate, the preparation of the product comprises a step of eliminating the excess gallium which has not been complexed by the compound according to the present invention. Where appropriate, the Ga68 solution is made less acidic in order to facilitate the coupling with NOTA.

It has also been sought to optimize the dose of gallium so as to limit the dose of radiation given to the patient, while at the same time obtaining good product effectiveness. Since the patient's exposure time is much shorter than with radionuclides with quite a long lifetime, such as technicium or indium, the dose of product with gallium injected may thus be much higher than with these radionuclides. The applicant has thus studied complex that are effective at a dose of radioactivity of the order of 1 to 1000 Curie/mol, in particular 1 to 10, 1 to 100, or even more than approximately 2000 to 3000 Curie/mol. It will also be possible to carry out several series of measurement, for example at a radioactivity dose of the order of 0.1 to 1000 Curie/mol per measurement, in the same patient imaging session. The radioactivity of the product is, for example, between 100 and 1000 MBq/nmol.

The present invention also concerns a diagnostic composition containing the Ga68 complex of the invention and a carrier agent. Advantageously the composition is intended for intravenous administration. More advantageously the carrier agent is chosen in the following group: water for injection, isotonic agent, pH buffer and mixture thereof. In particular pH buffer is the one described in WO 2010/092114.

The present invention also concerns a method of diagnostic of a disorder associated to a modified expression of the folate receptor wherein it comprises the following step:
a) administration of the composition of the invention to a patient in need thereof and
b) PET imaging said patient.

Advantageously the disorder is a cancers such as breast, cervical, colorectal, renal, nasopharyngal, endometrial or ovarian cancer, in particular ovarian or endometrial carcinoma or an inflammatory condition (vascular for instance). More particularly the disorder is ovarian cancer.

In a particular embodiment the present invention concerns, the compound of formula FOLATE-(LINKER)i-NOTA in which FOLATE, LINKER, i and NOTA are as described above.

The present invention concerns also the process of preparation of a Ga68 complex according to the present invention which comprises the step of labeling the compound FOLATE-(LINKER)i-NOTA according to the present invention with Ga68.

Advantageously the process according to the present invention comprises a prior step of preparation of the compound FOLATE-(LINKER)i-NOTA according to the present invention by coupling NOTA to FOLATE, wherein NOTA and FOLATE are as defined above.

In a particular embodiment the present invention concerns also a kit containing the compound FOLATE-(LINKER)i-NOTA according to the present invention and Ga68.

Advantageously Ga68 is in the form of a sterile gallium solution that has left the generator.

In order to improve the sterility of the device and, where appropriate, to meet CGMP standards, it is possible to lyophilize the compound of the invention (FOLATE-(LINKER)i-NOTA)), which is dissolved (for example using sterile water and a buffer such as sodium acetate), and the resulting solution is added to the gallium solution by the radiopharmacist. Other methods of preparing the compound of the invention may be carried out, the principle being to obtain a solution of said compound, the desired parameters of which (stability, reactivity with gallium, sterility, etc.) are suitable for gallium complexation.

As regards the generator itself, devices are sought which improve miniaturization and sterility, as described in WO 2005/084168, for example with the solution of gallium leaving the generator being collected in a pre-sterilized empty packaging, the packaging filled with the Ga68 solution then being used with the administration kit comprising the compound according to the present invention. In particular, it is sought to ensure sterility of the generator throughout its lifetime, which is close to that of germanium, therefore approximately one year. Suitable generators may also be of the Ti 44/SC44 type.

Automated and preferably sterile systems comprising, for example, the following are also studied:
  a part for producing the Ga68 (Ga68 generator producing a solution of Ga68, and, where appropriate, concentrating means, means for sterilizing the solution of Ga68, means for collecting the sterile solution of Ga68);
  a part for coupling the solution of Ga68 with the Ga68 compound of the invention (FOLATE-(LINKER)i-NOTA), at the outlet of which the solution of product to be injected into the patient is collected; where appropriate, this part comprises a solution of stabilizing additives (pH, excess NOTA, protective groups, etc.) and heating/cooling means;
  where appropriate, a part for administering the solution of product ready for injection.

The preparation process preferably includes an aspect of radioprotection of individuals, which is obtained, for example, by using appropriate packaging devices and/or injection devices (syringes, for example).

The complex of the applicant are also particularly useful for monitoring the efficacy of a drug intended to treat a disorder associated to a modified expression of the folate receptor, such as cancer, and in particular folate associated tumors such as breast, cervical, colorectal, renal, nasopharyngal, endometrial and ovarian cancer, notably ovarian cancer. Many drugs can thus be monitored, and the medical treatment can be optimized thanks to the use of the FOLATE-(LINKER)i-NOTA-Ga68 contrast agent of the applicant. For instance, in view of the imaging results obtained with the contrast agent after a first administration phase of the therapeutic treatment, the dose and timing of administration of a second or of successive ulterior steps of treatment can be managed and monitored. The therapeutic drugs can be:
  either drugs targeting folate receptors specifically: any drug known can be used, notably the therapeutic drugs having the formula of any FOLATE derivative described in the present application (in this situation, the drug is not coupled with a chelating moiety, or is coupled with a chelating moiety complexing a therapeutic radionuclide instead of Ga68), or any antibody known against folate receptors;
  and/or at least one drug known for its efficacy against cancers or inflammatory (vascular for instance) diseases that can be diagnosed by the folate complex of the applicant.

The invention also relates to a method of monitoring the efficacy of a drug intended to treat a disorder associated to a modified expression of the folate receptor in a patient in need thereof wherein it comprises the following step:
  a) administration of the composition of the invention to said patient and PET imaging the patient in order to obtain an in vivo image of the region of interest in which said disorder is visible;
  b) administration of said drug to said patient in order to treat said disorder;
  c) repeating step a);
  d) comparing the image obtained in step a) to the one obtained in step c) in order to determine the efficacy of said drug;
  e) if necessary adjusting the dosage or timing of administration of said drug.

This method can also be used for evaluating, and/or screening, the efficacy of a drug, and/or adjusting the dose and timing of a drug administration.

Advantageously step a) and c) consists in the successive following steps:
  (i) administration of the composition of the invention to said patient;
  (ii) allowing the administered complex of the invention to bind to folate receptor expressed by the pathologic area in which said disorder is visible;
  (iii) detecting the PET signals emitted by the NOTA moiety of the complex of the invention; and
  (iv) converting the signals detected in step (iii) into in vivo image representative of folate expression on the surface of the area cells of said pathologic area in said region of interest;

The invention also relates to a method of monitoring the efficacy of a drug, and/or adjusting the dose and timing of administration of a drug, and/or of identifying a patient likely to be responsive to a drug, this drug being advantageously a therapeutic drug intended to treat a subject suffering from a disorder associated to modified expression of folate receptor, said method comprising:
  1) imaging a pathologic area with a FOLATE-(LINKER)i-NOTA-Ga68 imaging agent of the application
  2) treating said subject with said drug;
  3) imaging a second time said pathologic area with the FOLATE-(LINKER)i-NOTA-Ga68 imaging agent of the application
  4) evaluate the efficacy of said treatment by comparing the imaging results obtained in step 1) and 3), i.e. before and after the treatment
  5) eventually adjusting the dose of the drug in view of said comparison Advantageously steps a) to f) are repeated several times corresponding to successive treatment phases of the patient, during a period typically of 1 month to 5 years to monitor and optimize the efficacy of the treatment.

The invention also relates to a method of optimizing the dose of an anti-cancer agent, the method comprising:
(a) administering a FOLATE-(LINKER)i-NOTA-Ga68 imaging agent of the application to a patient who has received at least one dose of an anti-cancer agent, either a folate receptor targeting drug or another anticancer drug
(b) imaging the pathologic area of interest in the patient;
(c) comparing the imaging result prior to treatment with the anti-cancer agent,
(d) wherein a change in the imaging result identifies the dose as an effective dose.

Typically the pathologic area is a cancerous area (in particular breast, cervical, colorectal, renal, nasopharyngal, endometrial or ovarian cancer, in particular ovarian or endometrial carcinoma) or an inflammatory area.

The following compounds and any of their derivatives shall be particularly preferred as a drug, alone or in association:
metotrexate
pemetrexed
folate agent from Endocyte, notably EC145, EC0489, EC0225
Antibodies against ovarian cancer, notably farletuzumab (at a dose notably preferably of 0.1-10 mg/Kg, notably 1-10 mg/Kg)
Platinium based anticancer drugs, including cisplatin, carboplatin, phosphaplatin
Drugs for ovarian cancer resistant to platinium drugs, including NKTR-102
Antiangiogenesis compounds active against ovarian cancer
Doxorucin compounds, notably doxorubicin liposomes
Trastuzamab (Herceptin)
Paclitaxel, and taxotere derivatives
Epithelone drugs
Anti-COX 2 drugs
Voloxicimab, bevacizumab
Imatinib
Sagopilone (ZK epothilone)
Pamitumumab
Gemcitamib
Anti HB-EGF antibodies
Anti EGF antibodies
Anti tyrosine kinase (EGFR, ErbB2, ErbB3, ErbB4) notably anti EGFR
Anti VEGFR, notably VEGFR tyrosine kinase inhibitors
Anti PARP (Poly ADP ribose polymerase inhibitors)
Anti src kinases (AZD0530)
Any compound or combination of compounds of the following table issued from Gynecologic Oncology 119 (2010), 151-156

For instance FOLATE-(LINKER)i-NOTA-Ga68 diagnostic agent of the applicant is used in combination with the therapeutic following protocols:
1) Farletuzumab at a dose notably preferably of 0.1-10 mg/Kg, notably 1-10 mg/Kg
2) Farletuzumab 2.5 mg/kg weekly intravenous infusion Carboplatin UAC 5-6 every 4 weeks for 6 cycles intravenous infusion Pegylated Liposomal Doxorubicin 30 mg/m2 every 4 weeks for 6 cycles intravenous infusion
3) Farletuzumab initial loading dose 5.0 mg/kg intravenous followed by 2.5 mg/kg intravenous for all subsequent doses every 2 weeks for up to 12 months.
4) Farletuzumab 1.25 mg/kg infusions will take place weekly during combination therapy and then as single agent maintenance until progression.
5) Farletuzumab in combination therapy with platinium drugs: At Week 1 of each 3-week cycle, farletuzmab given with one of three (3) acceptable chemotherapy regimens:
Carboplatin (area under the curve [AUC] 6) and paclitaxel (200 mg/m2)
Carboplatin (AUC 5) and pemetrexed (500 mg/m2)
Cisplatin (75 mg/m2) and pemetrexed (500 mg/m2); all protocol acceptable platinium containing regimens are administered on a three (3) weekly schedule for at least four (4), but no more than of six (6) cycles.

These treatments and imaging methods are advantageous with any specific imaging protocols in particular imaging sequences, apparatus, data acquisition and analysis processing.

Those skilled in the art understand that, in customary practice, different variants are possible for this mixture. Typically, the FOLATE-(LINKER)i-NOTA (not yet radiolabelled) is provided in the form of a concentrated aqueous solution, before the introduction of the buffer solution, and the acid eluate (pH around 2) of Ga68. For example, as illustrated hereafter, a volume of 0.4 ml or 0.6 nM Ga68 solution is added to the reactor which contains 1 ml of buffer solution and 20 µl of 1.2 M FOLATE-(LINKER)i-NOTA solution. However, it is understood that all the variants which give an equivalent result for the complexation are included in the present invention. For example, a greater amount of Ga68 solution at an appropriate dilution may be provided. For example, for reasons of FOLATE storage, the labeled NOTA is provided in buffer solution and not in an aqueous solution different than the buffer.

Various buffers or combinations of buffers can also be used as complexation buffer solution, in particular a combination of at least two buffers, for example acetate, lactate, citrate, succinate, carbonate, a mixed lactic-succinic or lactic-tartaric buffer, in proportions of advantageously 90/10, 80/20, 70/30, 60/40, 50/50 for combinations of two buffers.

Advantageously, the buffer solution is a solution at from 0.05 to 1.5 M with respect to buffer, preferably from 0.1M to 1M with respect to buffer; advantageously 0.1 to 0.5 M, for instance 0.1 to 0.3 M.

Advantageously, the concentration of the radiolabeled FOLATE-(LINKER)i-NOTA-Ga68 in the injectable buffer solution is between 0.1 and 100 µM, for example 0.5 to 20 µM, in particular 1 to 10 µM.

As regards more particularly the methods of imaging of the compounds studied, the PET imaging with Ga68 may, moreover, be coupled with certain specific methods of MRI imaging.

In particular, the combination of PET (or PET CT with PET for the functional imaging and the CT scan for the anatomical imaging) and of MRI makes it possible to combine the very high sensitivity of PET (but which has a resolution which is not as good as MRI) with the very high resolution of MRI (but which has a sensitivity which is not as good as PET). In order to improve the contrast, at least one contrast product FOLATE-(LINKER)i-NOTA of the invention for PET, preferably with Ga68, which makes it possible to detect all the tumor zones and metastases over the entire body, and at least one contrast product for MRI intended to visualize with a high resolution one or more zones detected with the PET, may be administered simultaneously or with a delay between them. It is also possible to realize first a PET examination and afterwards another modality exam such as MRI and/or CT scan.

Automated processes will be particularly advantageous for such an imaging combination, in order to optimize the administration, the reading and the image analysis, using, where appropriate, automatic contrast product injection devices. It will be possible, for example, according to the results of the PET detection, to automatically zoom into one or more zones of interest pinpointed with the PET, with or without the injection of contrast product. For example, a specific contrast product vectorized for PET with Ga68 according to the invention and a contrast product vectorized for MRI with gadolinium may be used, the biovectors being identical or different, with for example the biovector of the PET product being capable of localizing an angiogenesis in all tumors, and the biovector of the MRI product being capable of studying with precision the localization and/or the characterization of the progression of specific tumoral zones in various biological territories.

The invention thus also relates to an imaging method comprising:

a) the administration of at least one FOLATE-(LINKER)i-NOTA-Ga68 contrast product for detecting by PET imaging at least one zone of diagnostic interest;

b) the administration of at least one contrast product for MRI or XR scan, intended to specifically analyze the zone(s) of diagnostic interest detected in a).

Also MRI and or RX scanner can be done before PET.

For the purpose of the present invention, the expression "alkyl group, advantageously $C_1$-$C_{10}$" is intended to mean any linear or branched alkyl group advantageously containing from 1 to 10 linear or branched carbon atoms, in particular methyl, ethyl, n-propyl, isopropyl, n-butyl, isobutyl, sec-butyl, t-butyl, n-pentyl and n-hexyl groups. Advantageously it is a methyl group.

For the purpose of the present invention, the expression "alkenyl group, advantageously $C_2$-$C_6$" is intended to mean any linear or branched alkenyl group advantageously containing from 2 to 6 linear or branched carbon atoms, in particular the vinyl group.

For the purpose of the present invention, the expression "alkynyl group, advantageously $C_2$-$C_6$" is intended to mean any linear or branched alkynyl group advantageously containing from 2 to 6 linear or branched carbon atoms, in particular an ethynyl group.

For the purpose of the present invention, the expression "alkoxy group, advantageously $C_1$-$C_{10}$" is intended to mean any linear or branched alkoxy group advantageously containing from 1 to 10 linear or branched carbon atoms, in particular the $OCH_3$ group.

For the purpose of the present invention, the term "aryl group" is intended to mean one or more aromatic rings containing from 5 to 8 carbon atoms, that may be attached or fused, optionally substituted with halogen atoms, alkyl groups as defined above or the nitro group. In particular, the aryl groups may be monocyclic or bicyclic groups, preferably phenyl, naphthyl, tetrahydronaphthyl or indanyl. It is advantageously a phenyl group.

For the purpose of the present invention, the term "heteroaryl group" is intended to mean any hydrocarbon-based aromatic group having from 3 to 9 atoms containing one or more heteroatoms, such as, for example, sulfur, nitrogen or oxygen atoms, and possibly bearing one or more substituents, such as, for example, a $C_1$-$C_7$ alkyl group as defined above, a $C_2$-$C_7$ alkenyl group as defined above or a halogen. Examples of heteroaryl groups are furyl, isoxazyl, pyridyl or pyrimidyl groups.

The term "polyalkoxyalkylene" is intended to mean a polyalkoxy($C_2$-$C_3$)alklylene (i.e. polyoxyethylenes and polyoxypropylenes), in particular polyethylene glycol, PEG, and $C_1$ to $C_3$ monoethers and monoesters thereof, having a molecular mass of preferably 1000 to 2000.

The detailed examples illustrate the invention not imitatively.

EXAMPLE 1

Synthesis of Folate Dideaza-NODAGA-Ga68

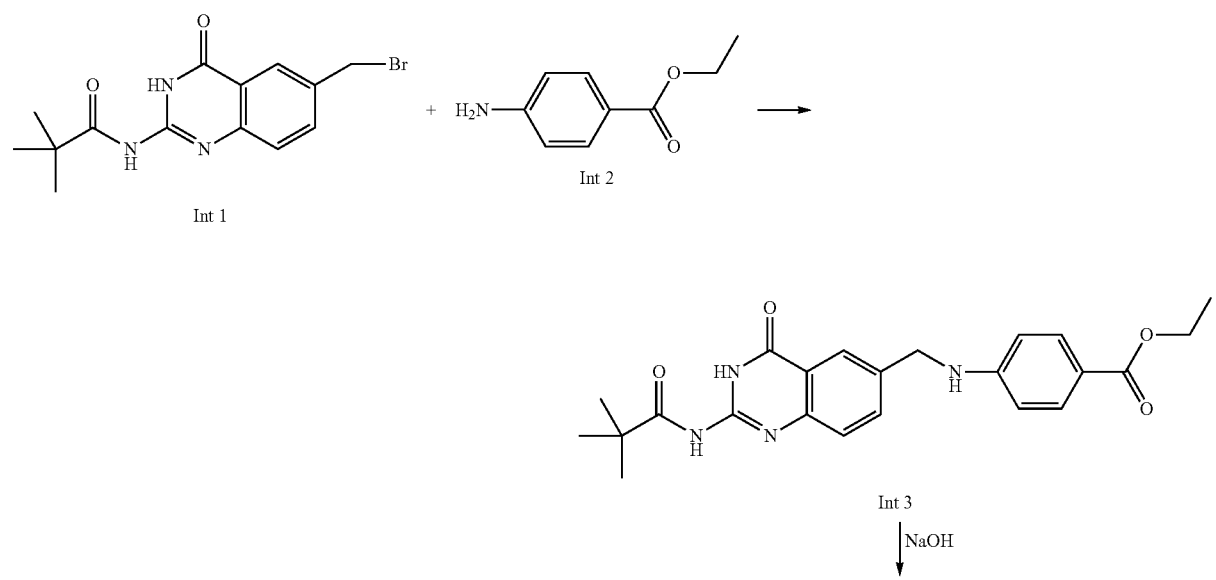

-continued
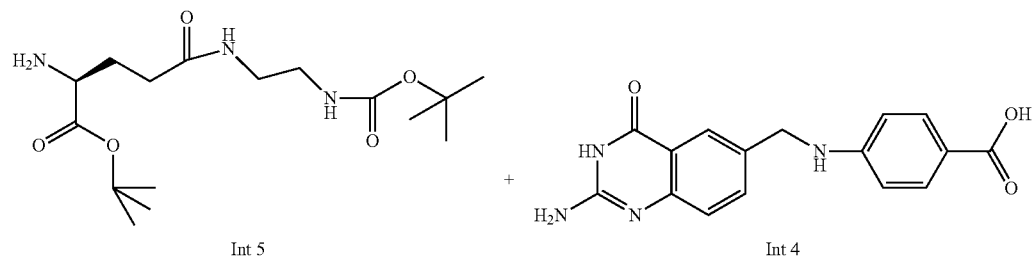
Int 5 + Int 4
↓ DCC/NHS
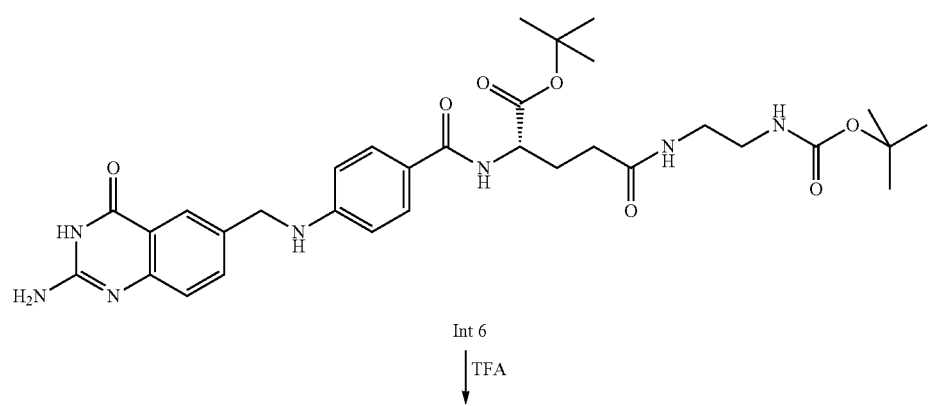
Int 6
↓ TFA
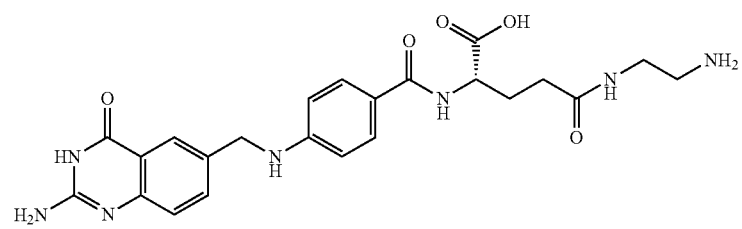
Int 7
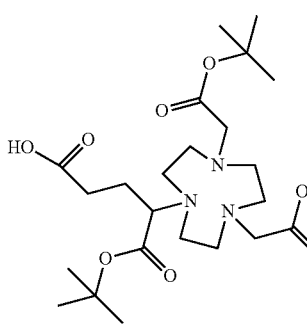
Int 8
↓ DCC/NHS

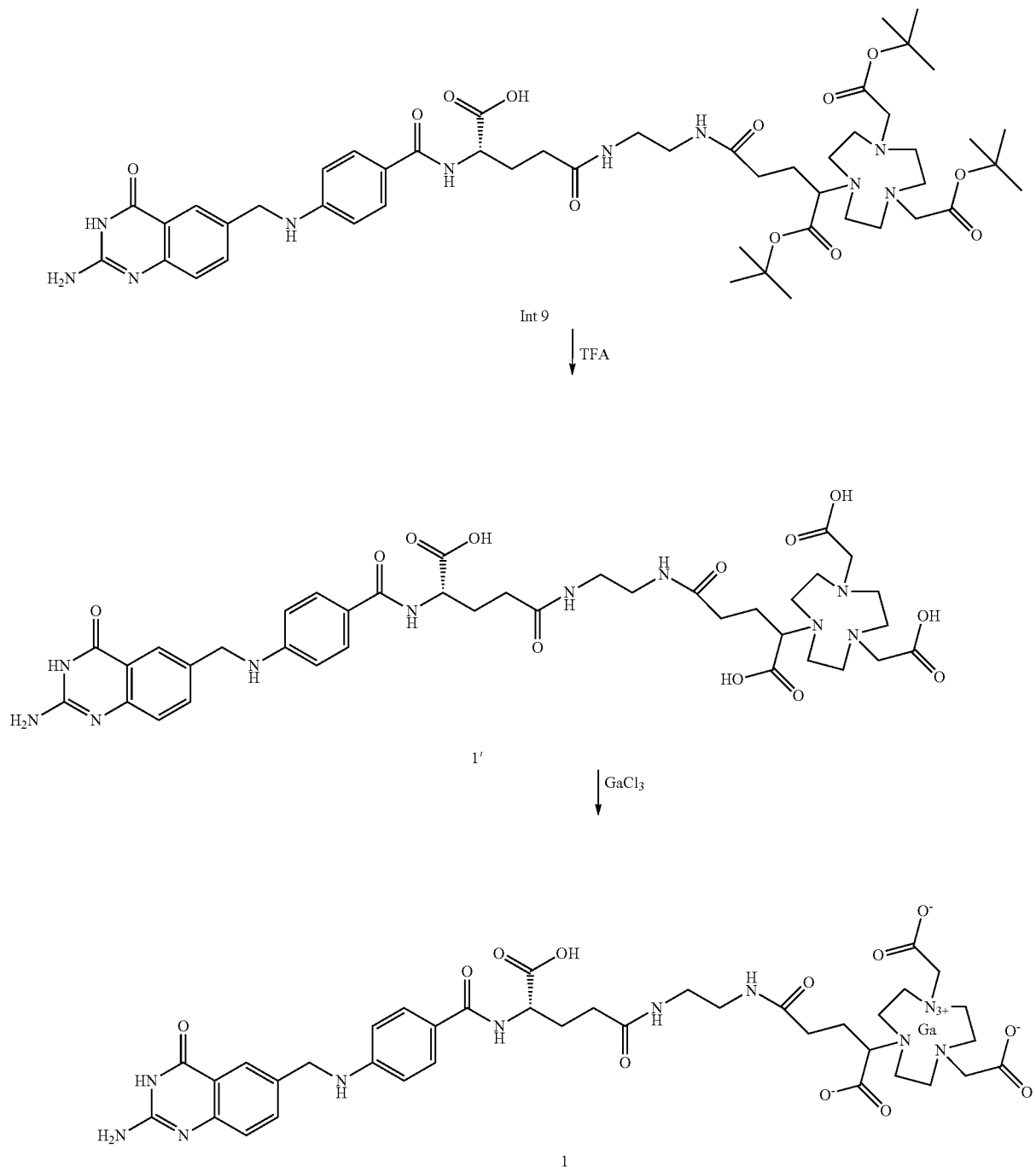

Stage 1:

0.5 g of intermediate 2 is dissolved in 20 ml of CH₃CN, in the presence of 0.6 g of K₂CO₃. A suspension of the brominated derivative (Int. 1) in 20 ml of CH₃CN is added thereto. The reaction medium is maintained at reflux, under argon, with vigorous magnetic stirring, for 18 H. After a return to ambient temperature, the reaction medium is filtered. The insoluble material is taken up in 20 ml of water and then filtered. The filtrate is evaporated under pressure. The residue obtained is taken up in Et₂O and is then filtered. 1.2 g of product are obtained. [M+H]+=423.16

Stage 2:

0.6 g of the intermediate obtained in the previous stage (Int 3) is suspended in 2.4 ml of ethanol. Dissolution is complete after the addition of 6 ml of 1M NaOH. The reaction medium is stirred for 1H30 at 70° C. After a return to ambient temperature, the medium is brought to pH 1 by adding HCl 6N. The suspension obtained is filtered and then washed thoroughly with water and subsequently with ethanol. After drying, 0.35 g of product is obtained (yield=80%). $[M+H]^+=311.10$ Stage 3:

Int. 4 (1.8 mmol) and Int. 5 (1.8 mmol) are dissolved in DMF, at ambient temperature, under dry conditions ($CaCl_2$ track). 1.4 eq of HOBT (2.5 mmol) and then 1.4 eq of EDCI (2.5 mmol) are added to the reaction medium. After reaction overnight at ambient temperature, the reaction medium is precipitated from 250 ml of water. After filtration, the residue is washed with water and then dried under vacuum; 0.85 g of yellow crystals is obtained with a yield of 81%. $[M+H]+=638.30$ Stage 4:

0.266 mmol of intermediate obtained in the previous stage (int 6) is dissolved in 1.8 ml of TFA. The reaction medium is left at ambient temperature for 1H and is then evaporated. The product is obtained by crystallization from 25 ml of $Et_2O$. 180 mg of yellow crystals are obtained, which are purified in an open column on RP2 silica, elution being carried out with water (TFA 0.05%)/$CH_3CN$. After freeze-drying, 50 mg of white product are obtained (yield 31%). BP: $[M+H]^+=482.22$, $[M+2H]^{2+}=241.68$ Stage 5

Formation of the Activated Ester:

After 75 mg of $NODAGA(tBu)_3$ (Int 8) have been dissolved in 2 ml of $CH_2Cl_2$, mg (1 eq) of NHS and then 28 mg (1 eq) of DCC are added. After reaction for half an hour at ambient temperature, the DCU formed is filtered through Whatman paper and the filtrate is concentrated to a final volume of approximately 0.5 ml.

Amidation:

50 mg of intermediate obtained in the previous stage (Int 7) are dissolved in 2.5 ml of DMSO in the presence of 2 eq of $NEt_3$ (40 µl). The activated ester, in solution in $CH_2Cl_2$ is added thereto. After reaction for 1H, the reaction medium is precipitated from 25 ml of $Et_2O$. The product obtained is used in the purification by flash chromatography (Merck SVF D26-RP18 25-40 µm-31 g silica cartridge), after having been solubilized in 50/50 (aqueous eluant phase (TFA pH2.8)/$CH_3CN$). After freeze-drying, 24 mg of white crystals are obtained (yield 28.4%). BP: $[M+H]^+=1007.5$, $[M+2H]^{2+}=504.44$ Stage 6

24 mg of intermediate obtained in the previous stage (Int 9) are solubilized in 1 ml of TFA. After reaction for 6 h at ambient temperature, the reaction medium is evaporated and taken up in 25 ml of $Et_2O$. 10 mg of crystals are obtained.

Stage 7

20 µl of a 1 mg/ml aqueous solution of the compound obtained at the stage 6 (compound 1') and 1 ml of sodium lactate buffer 0.5M pH3.9 are introduced in the reaction vial. Then 400 µl of a solution of $^{68}GaCl_3$ in a mixture HCl 0.05M/acetone are added. The reaction mixture is incubated at room temperature for 15 min. The reaction vial is washed with 6 ml of water and the reaction mixture is transferred into the C-18 column which was preconditioned with 1 ml ethanol and 1 ml ultra-pure water. The final product is eluted from the cartridge with 1 ml of a 50% ethanol/water solution.

The final product (compound 1) is passed through a 0.22 µm Millipore filter and is diluted with NaCl 0.9% up to 6 ml.

Similar procedure is used for acetate, HEPES, lactate, succinate, phosphate, maleate, malate buffers.

EXAMPLE 2

Synthesis of folate-NODAGA-Ga68 a) Compound of Formula:

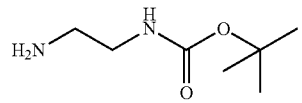

20 g (91.7 mmol) of $Boc_2O$ are dissolved in 40 ml of $CH_2Cl_2$. Then a solution of 22 g (366.6 mmol) of diaminoethane in 200 ml of $CH_2Cl_2$ is added dropwise. The reaction vial is mixed at room temperature for 2 hours. First, the product is purified by extraction with water. The organic layer is dried over $Na_2SO_4$ and filtered. Then it is purified by flash chromatography on silica with a gradient of $CH_2Cl_2$/Methanol. 4 g of a yellow oil are obtained. m/z=161 (ES+)

b) Compound of Formula:

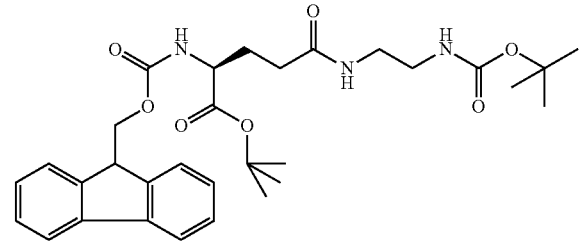 [SMILES: CC(C)(C)OC(=O)NCCNC(=O)CC[C@H](NC(=O)OCC1c2ccccc2-c2ccccc21)C(=O)OC(C)(C)C]

10.27 g (24 mmol) of Fmoc-Glu-OtBu are dissolved in 300 ml of $CH_2Cl_2$ 2.8 g of NHS and 4.98 g de DCC are introduced. After 45 minutes, the reaction mixture is filtered and added dropwise in a solution of 3.869 g of the product obtained in a) dissolved in 50 ml of $CH_2Cl_2$. After 2 hours at room temperature the product is first purified by extraction with water. The organic layer is dried over $Na_2SO_4$ and filtered. Then it is purified by flash chromatography on silica with a gradient of $CH_2Cl_2$/acetone. 7 g of product are obtained. m/z=568 (ES+)

c) Compound of Formula:

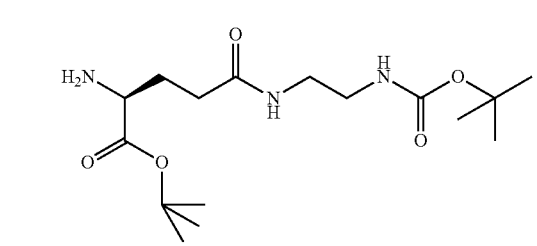 [SMILES: CC(C)(C)OC(=O)NCCNC(=O)CC[C@H](N)C(=O)OC(C)(C)C]

6.5 g (11.4 mmol) of the product obtained in b) are dissolved in 91 ml of acetonitrile. A solution obtained with 19.5 ml of piperidine and 78 ml of acetonitrile) is added dropwise. After 2 hours at room temperature under argon atmosphere the reaction mixture is evaporated and purified by flash chromatography on silica with a gradient of $CH_2Cl_2$/methanol. 3.65 g of oil are obtained. m/z=346 (ES+)

d) Compound of Formula:

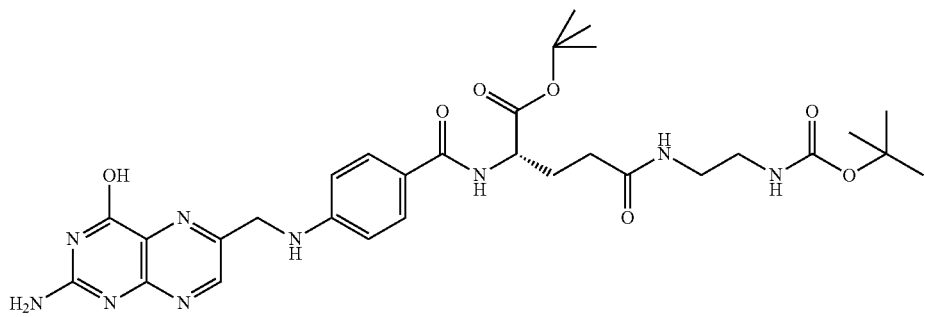 [SMILES: CC(C)(C)OC(=O)NCCNC(=O)CC[C@H](NC(=O)c1ccc(NCc2cnc3nc(N)nc(O)c3n2)cc1)C(=O)OC(C)(C)C]

3.3 g (10.5 mmol) of pteroic acid and 3.65 g of the product obtained in c) are dissolved in 335 ml of DMSO under argon. 3.038 g of EDCI and 1 g of HOBT are added. The reaction mixture is heated to 40° C. overnight then precipitated in water. The residue is filtered and washed with first water then Et$_2$O. 6 g of red powder are obtained.

m/z=640 (ES+)

e) Compound of Formula:

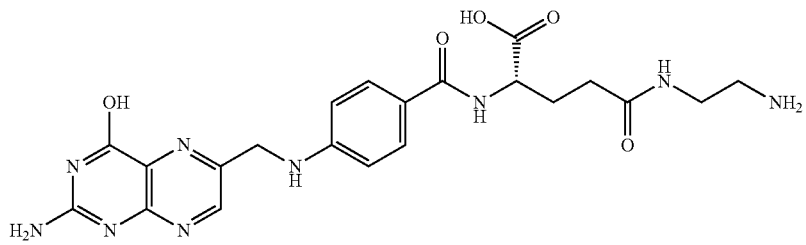 [SMILES: NCCNC(=O)CC[C@H](NC(=O)c1ccc(NCc2cnc3nc(N)nc(O)c3n2)cc1)C(=O)O]

6 g (9.3 mmol) of the product obtained in d) are dissolved in 74 ml of TFA. After 1 hour at room temperature the reaction mixture is precipitated in 800 ml of Et$_2$O. After filtration, 4.5 g of a yellow powder are obtained. m/z=484 (ES+)

f) Compound of Formula:

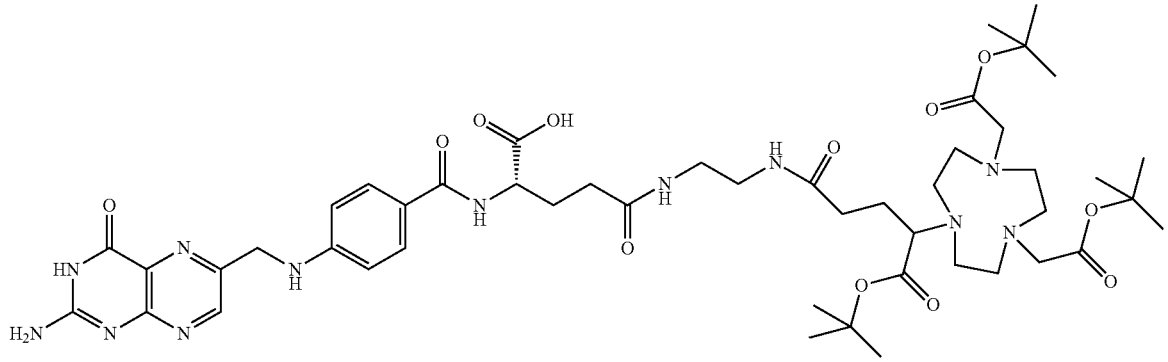 [SMILES: CC(C)(C)OC(=O)CN1CCN(CC(=O)OC(C)(C)C)CCN(C(CCC(=O)NCCNC(=O)CC[C@H](NC(=O)c2ccc(NCc3cnc4nc(N)[nH]c(=O)c4n3)cc2)C(=O)O)C(=O)OC(C)(C)C)CC1]

Applying the same procedure as that described at the step 5 of the example 1 starting from:

85 mg of the compound obtained in e) and 75 mg of NOTAGA(tBu)$_3$ 15 mg of the compound are obtained. m/z (ES+)=1009 g) Compound of Formula (Compound NODAGA-Folate) (Compound 2'):

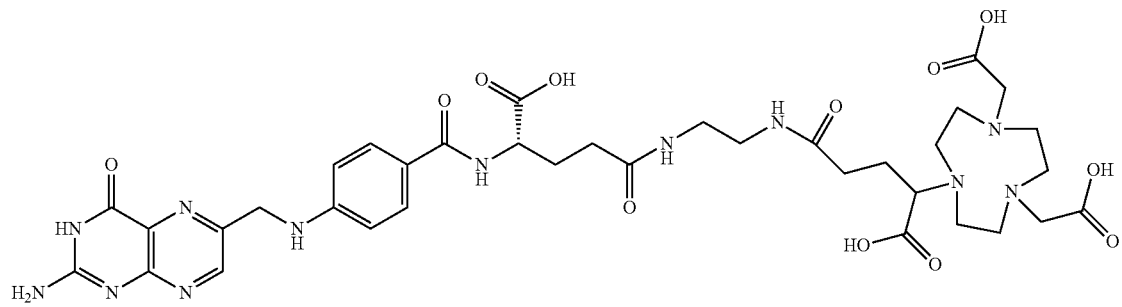 [SMILES: Nc1nc2ncc(CNc3ccc(C(=O)N[C@@H](CCC(=O)NCCNC(=O)CCC(C(=O)O)N4CCN(CC(=O)O)CCN(CC(=O)O)CC4)C(=O)O)cc3)nc2c(=O)[nH]1]

Applying the same procedure as that described at the step 6 of the example 1 starting from 20 mg of the compound obtained in f)

4 mg of the compound are obtained. m/z (ES+)=841 h) Compound of Formula (compound NODAGA-folate-Ga68) (Compound 2):

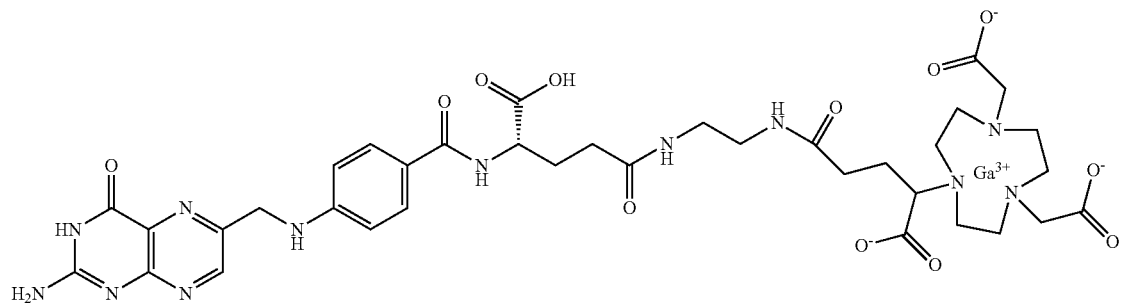

20 μl of a 1 mg/ml aqueous solution of the compound obtained at g) and 1 ml of buffer (notably sodium acetate 0.5 M pH 3.5 to 4 or other buffers such as lactate or succinate buffer 0.5M) are introduced in the reaction vial. Then 400 μl of a solution of $^{68}GaCl_3$ in a mixture HCl 0.05M/acetone are added. The reaction mixture is incubated at room temperature for 15 min. The reaction vial is washed with 6 ml of water and the reaction mixture is transferred into the C-18 column which was preconditioned with 1 ml ethanol and 1 ml ultra-pure water. The final product is eluted from the cartridge with 1 ml of a 50% ethanol/water solution.

The final product is passed through a 0.22 μm Millipore filter and is diluted with NaCl 0.9% up to 6 ml.

EXAMPLE 3

Other Compounds FOLATE-LINKER of the Invention Comprising Different LINKER

A series of folic acid derivatives (FOLATE-LINKER) (No. 7, 8 or 9) are prepared, the structures of which are given in the table below.

| No. | Structure | MW |
|---|---|---|
| 7 | 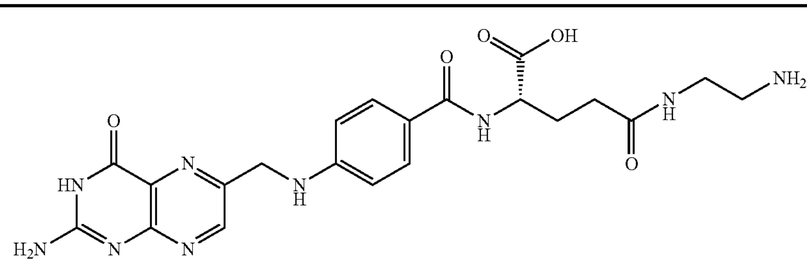 | 483.49 |

| No. | Structure | MW |
|---|---|---|
| 8 | 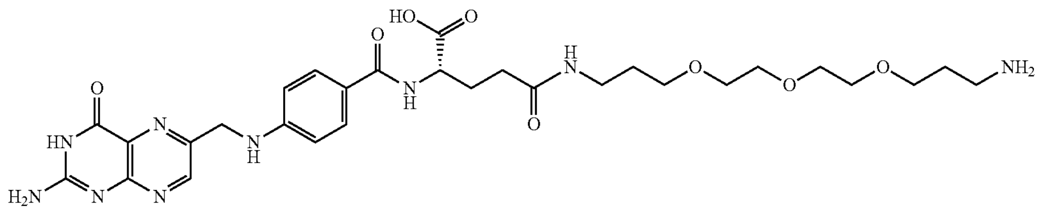 [SMILES: NCCCOCCOCCOCCCNC(=O)CC[C@H](NC(=O)c1ccc(NCc2cnc3nc(N)[nH]c(=O)c3n2)cc1)C(=O)O] | 643.71 |
| 9 | 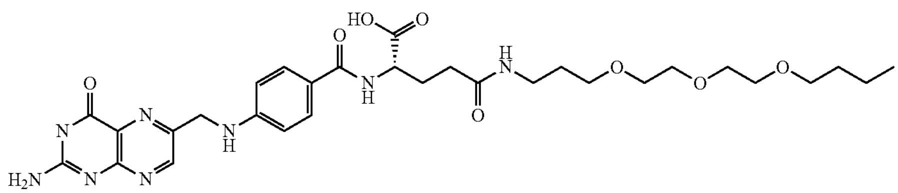 | 1244.42 |

Synthesis of the Folic Acid Derivatives (FOLATE LINKER):

The synthesis of derivative No. 8 is described in example 11 of document WO 2004/112839, pages 105 to 108.

The synthesis of derivative No. 7 is carried out according to the same protocol as for derivative 8, with the exception of the final stage, where the 4,7,10-trioxa-1,13-tridecanediamine is replaced with ethylenediamine The synthesis of derivative No. 9 is carried out using the derivative 8 which is condensed to the linker whose structure is the following

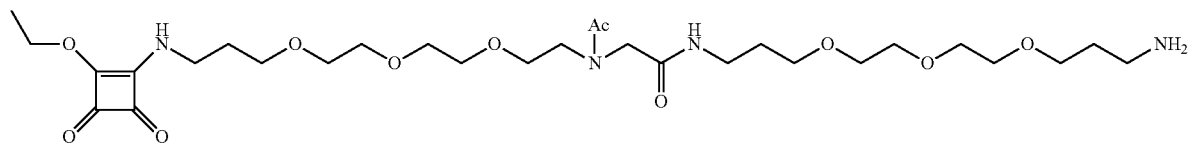 [SMILES: CCOc1c(NCCCOCCOCCOCCN(CC(=O)NCCCOCCOCCOCCCN)C(C)=O)c(=O)c1=O]

Briefly, the synthesis of this linker is carried out in 4 stages using the 4,7,10-trioxa-1,13-tridecanediamine monoBoc (compound a) of example 15 in the specific patent).
Stage 1:

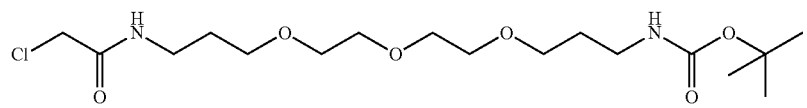 [SMILES: CC(C)(C)OC(=O)NCCCOCCOCCOCCCNC(=O)CCl]

10 g of 4,7,10-trioxa-1,13-tridecanediamine monoBoc (31.2 mmol) are dissolved at −5° C. (by means of a bath of acetone and ice) in 50 ml of $CH_2Cl_2$. 5 g of $K_2CO_3$ (36.2 mmol) dissolved in 50 ml of water and 5 g of chloroacetyl chloride (44.2 mmol) dissolved in 50 ml of $CH_2Cl_2$ are added simultaneously, dropwise, under cold conditions. The reaction medium is stirred at AT for 1 hour. The organic phase is washed with water until neutral pH and then filtered and evaporated to dryness.
m=11.2 g.
$ES^+$: m/z (z=1)=397.3.

Stage 2:

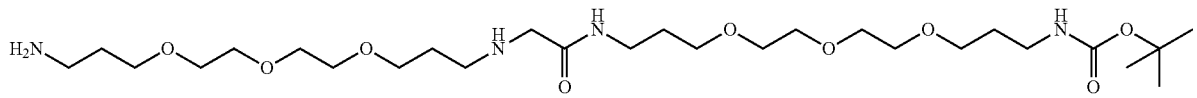 [SMILES: CC(C)(C)OC(=O)NCCCOCCOCCOCCCNC(=O)CNCCCOCCOCCOCCCN]

6.8 g of 4,7,10-trioxa-1,13-tridecanediamine are dissolved in 50 ml of $CH_3CN$ in the presence of 0.85 g of $K_2CO_3$. 6.2 mmol of the compound derived from stage 1, dissolved in 25 ml of $CH_3CN$, are added, dropwise, to this solution. The reaction medium is refluxed for 2 h. After returning to ambient temperature, the reaction medium is filtered and then evaporated. The residue obtained is dissolved in 50 ml of $CH_2Cl_2$ and washed with 4×20 ml of water. The organic phase is dried over $Na_2SO_4$ and then purified on silica with a 50/50 then 30/70 mixture of $CH_2Cl_2$/MeOH. m=1.8 g (yield 50%).

$ES^+$ M/z=581 (z=1) and M/z=291.3 (z=2).

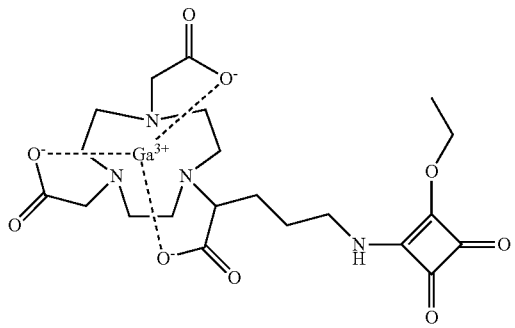

Stage 3:

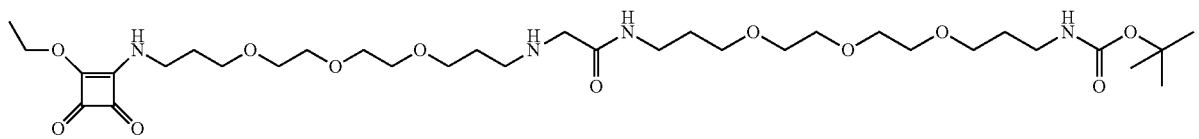 [SMILES: CCOc1c(NCCCOCCOCCOCCCNCC(=O)NCCCOCCOCCOCCCNC(=O)OC(C)(C)C)c(=O)c1=O]

0.25 g of the compound derived from the preceding stage is solubilized in 1.5 ml of $CH_2Cl_2$. 57.5 µl of diethyl squaric acid are added. The reaction medium is stirred for 18 h at ambient temperature. The product is not isolated.

$ES^+$ M/z=706 (z=1) and M/z=354 (z=2).

Stage 4:

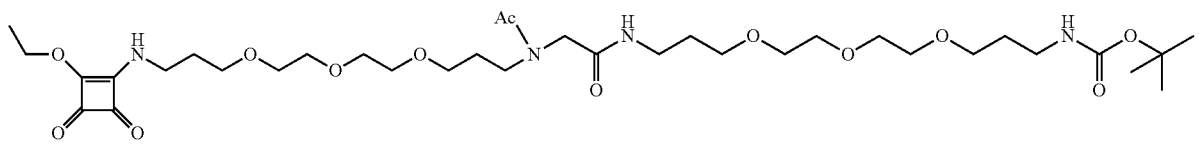 [SMILES: CCOc1c(NCCCOCCOCCOCCCN(CC(=O)NCCCOCCOCCOCCCNC(=O)OC(C)(C)C)C(C)=O)c(=O)c1=O]

40.6 µl of $Ac_2O$ are added to the reaction medium derived from stage 3, and the whole is stirred for 5 minutes at ambient temperature before being purified on silica, elution being carried out with $CH_2Cl_2$/EtOH (9/1). m=0.27 g (translucent oil).

$ES^+$ M/z=748 with z=1.

Stages 1 and 2 corresponding to the coupling of folic acid derivatives No. 7, 8 or 9 to the acid derivative of example 8, and to the deprotection, are carried out according to the same protocol as that described in example 9 of WO2007/042504.

EXAMPLE 4

Other Compounds LINKER-NOTA of the Invention

This example illustrates the synthesis of a NOTA-LINKER intermediate. In this example Ga68 is added to the NOTA not yet linked to the FOLATE; however preferably Ga68 will be added to the NOTA-LINKER-FOLATE compound.

Gallium complex of 2-(4,7-biscarboxymethyl[1,4,7]triazonan-1-yl)-5-(2-ethoxy-3,4-dioxocyclobut-1-enylamino) pentanoic acid This compound is prepared according to the following synthesis scheme, starting from commercial triaza-1,4,7-cyclononane

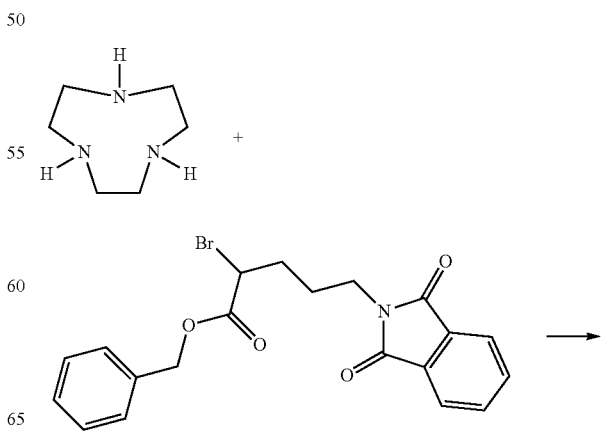

-continued

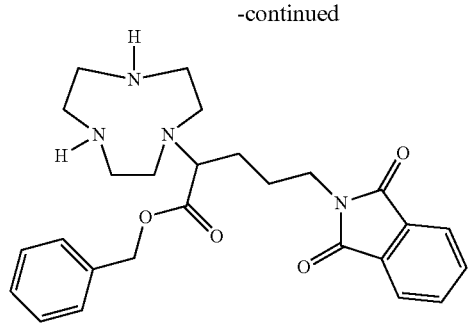

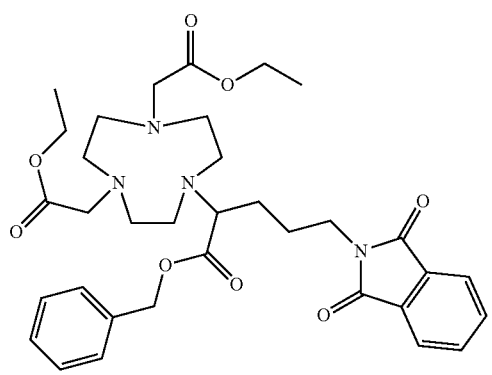

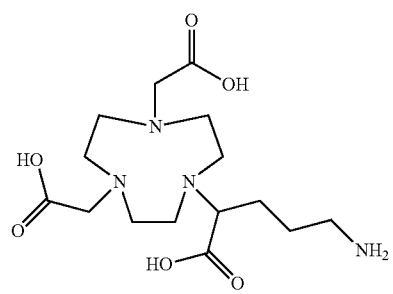

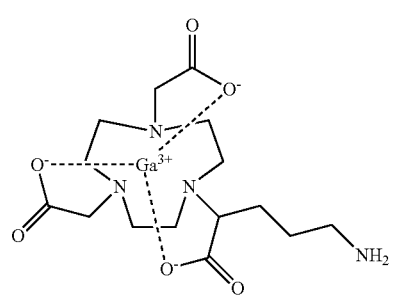

EXAMPLE 5

2-(4,7-Bis-tert-butoxycarbonylmethyl[1,4,7]triazonan-1-yl)-5-(2-ethoxy-3,4-dioxocyclobut-1-enylamino)pentanoic acid tert-butyl ester Stage 1:

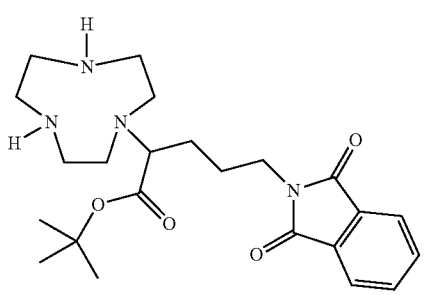

Mw = 430.55 g/mol 10 g of triaza-1,4,7-cyclononane (77.4 mmol) are dissolved in a water-acetonitrile mixture (170 ml of acetonitrile and 7 ml of water). After the addition of 10.7 g of $K_2CO_3$, 29.6 g of 2-bromo-5-(1,3-dioxo-1,3-dihydroisoindol-2-yl)pentanoic acid tert-butyl ester in solution in 50 ml of $CH_3CN$ are added dropwise. After stirring for 24 h at 25° C., the reaction medium is filtered, washed with $CH_3CN$, and then concentrated. After acid-base washes, 20 g of product are obtained.

Mass spectrum: Mode $ES^+$ m/z=431.5 with z=1.

Stage 2:

same protocol as in stage 2 of example 23 of WO2007/042504.

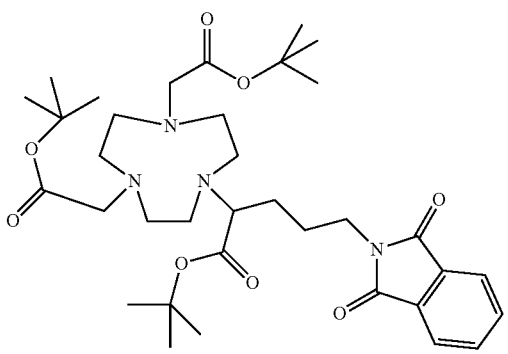

Mw = 658.84 g/mol

Stages 3 and 4:
same protocol as in stages 3 and 4 of example 17 of WO2007/042504.
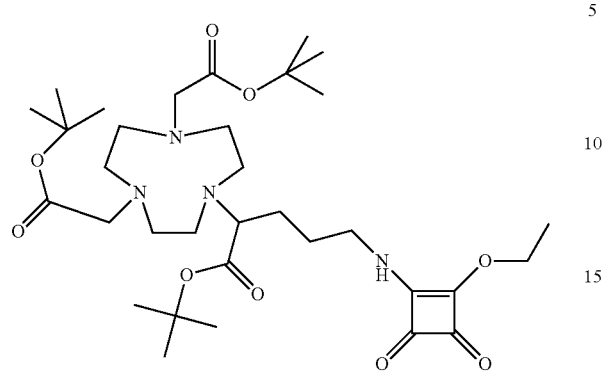
Mw = 652.84 g/mol
EXAMPLE 6
The compound of example 5 was coupled to a series of folic acid derivatives, the sequences of which are described in example 3, according to the same protocol as that described in example 19 of WO2007/042504.

| No. | Structure | MW |
|---|---|---|
| 7 | 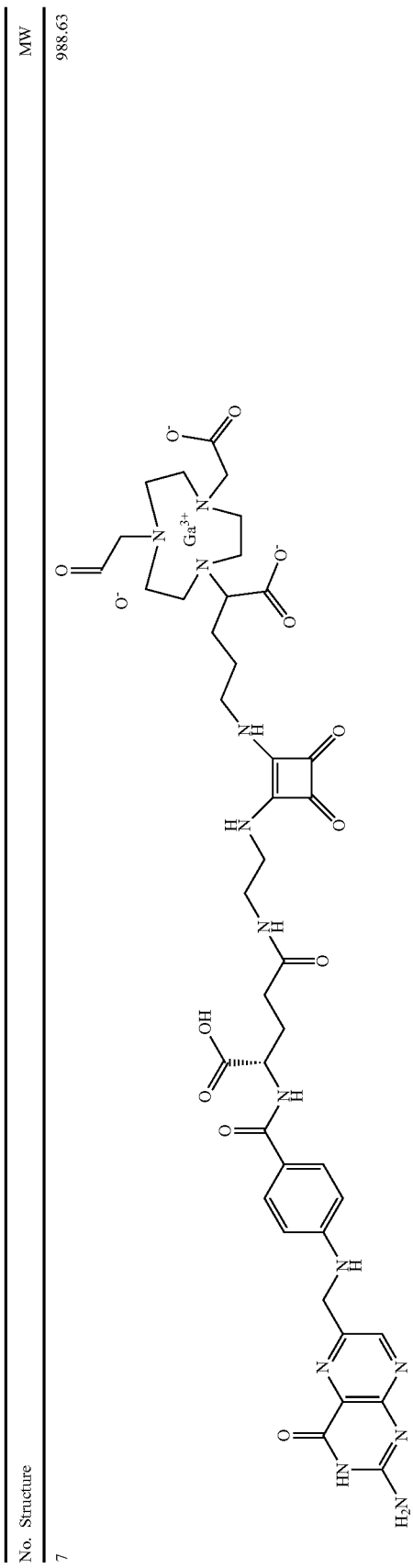 | 988.63 |
| 8 | 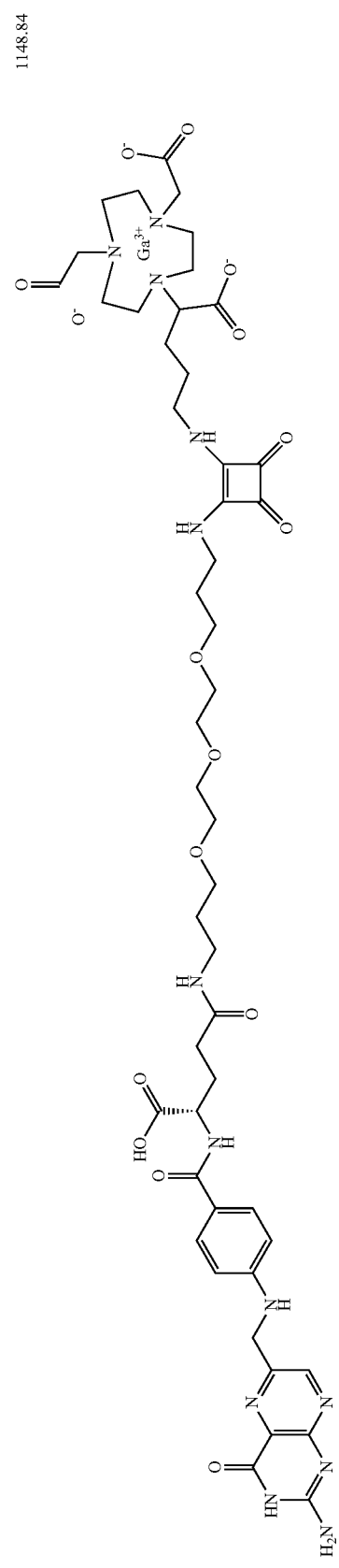 | 1148.84 |

-continued
| No. | Structure | MW |
|---|---|---|
| 9 | 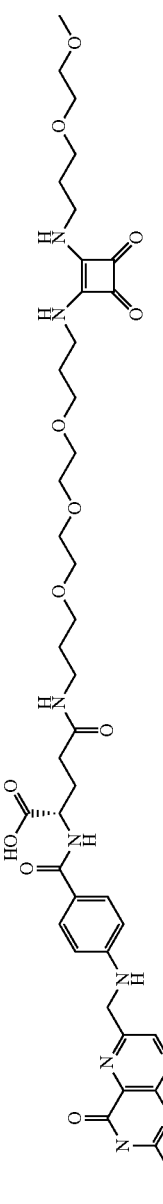 | 1749.56 |

EXAMPLE 7

In Vivo Study of NODAGA-LINKER-FOLATE—in a Mice Model Bearing KB Tumors

The new folate derivative, NODAGA-LINKER-FOLATE-Ga68 (compound 2) of example 2 step g, complexed with Gallium 68 according to the present invention was evaluated in vivo.

Nude mice bearing KB-tumors were used for this study.

For biodistribution up to 24 hours, NODAGA-LINKER-FOLATE-Ga67 (compound 2' of example 2 step g, complexed with Gallium 67) was used because of its longer half-life compared with the NODAGA-LINKER-FOLATE-68Ga Protocol The NODAGA-LINKER-FOLATE derivative was labeled with $^{68}$Ga using the Modular-Lab automatic system by Eckert & Ziegler.

NODAGA-LINKER-FOLATE-Ga68 compound (compound 2) was obtained in radiochemical purity preferably >92 to >98%. It was diluted with 0.9% NaCl at a concentration of 4 nmol/ml and this solution was injected to the mice (100 µl/0.4 nmol/mouse).

The NODAGA-LINKER-FOLATE derivative was labeled with $^{67}$Ga by incubation at RT with 37 MBq of $^{67}$GaCl$_3$ in HEPES buffer. NODAGA-LINKER-FOLATE-Ga67 compound was obtained in radiochemical purity preferably >92 to >98%. It was diluted with 0.9% NaCl at a concentration of 4 nmol/ml and this solution was injected to the mice (100 µl/0.4 nmol/mouse).

One week before the tumor cell inoculation all mice were put under a folate low diet (SAFE company, semi-synthetic product with 50 µg/kg of folate) until the end of the study.

At D0, the tumor inoculation was performed as follow: One million ($10^6$) of KB tumor cells (FR+) resuspended at $1 \times 10^7$ cells/ml in sterile PBS 0.01M, pH 7.4, were subcutaneously inoculated in the right flank of the nude mice in a volume of 100 µl. The tumors were allowed to grow for 8-9 days. For the in vivo evaluation the mice were grouped in groups of 3 mice per group.

At D8 biodistribution studies and PET/CT images were performed for NODAGA-folate-Ga68 (compound 2) in 2 groups of mice as follow:

1 group: injection with NODAGA-LINKER-FOLATE-Ga68 (compound 2) (0.4 nmol/2 MBq/100 µl/mouse)

1 group: injection of Alimta (400 µg/100 µl/mouse) 1 h before the injection of NODAGA-LINKER-FOLATE-Ga68 (compound 2)

Time point: 1 h p.i.

At D9 biodistribution studies were performed for the $^{67}$Ga-NODAGA-LINKER-FOLATE (compound 2' complexed by Ga67) in groups of mice as follow:

3 groups: injection with $^{67}$Ga-NODAGA-LINKER-FOLATE (compound 2' complexed by Ga67) (0.4 nmol/10 µCi/100 µl/mouse)

1 group: injection of Folic acid (40 nmol/100 µl/mouse) 5 min before the injection of $^{67}$Ga-NODAGA-LINKER-FOLATE (compound 2' complexed by Ga67)

1 group: injection of Alimta (400 µg/100 µl/mouse) 1 h before the injection of $^{67}$Ga-NODAGA-LINKER-FOLATE (compound 2' complexed by Ga67)

Time points: 2 h, 4 h, 4 h (blocking with FA), 4 h (kidney blocking with Alimta), 24 h p.i.

Results

With the NODAGA-LINKER-FOLATE-Ga68, the results are indicated in the following table 1 and in FIG. 1.

With the NODAGA-LINKER-FOLATE-Ga67, the results are indicated in the Table 2

The maximum tumor uptake was observed at 2 h p.i., which remains high even at 24 h p.i. The tumor uptake is specific as the blocking experiment with folic acid showed.

The kidney uptake was significantly reduced with the use of Alimta (compound known to target folate receptors), while the tumor uptake remained the same Alimta can be used for kidney blocking and for the improvement of tumor:kidney ratio.

High uptake was observed in the parotid gland (the largest of the salivary glands) with NODAGA-LINKER-FOLATE-Ga68 (compound 2). This was not the case in normal mice, where no folate-free diet had been used.

TABLE 1

Results with NODAGA-LINKER-FOLATE-Ga68 (compound 2)

| | |
|---|---|
| Radioligand | NODAGA-LINKER-FOLATE-Ga68 (compound 2) |
| Animals | Female nude mice (15-19 gr) under folate-free diet, bearing KB-tumors |
| Injection amount | 2 MBq/0.4 nmol/100 µl/mouse |
| Kidney blocking | Alimta 400 µg/100 µl/mouse, 1 h pre-injection |
| Groups: | Group 1: 3 mice injected with Alimta 1 h before injection of NODAGA-LINKER-FOLATE-Ga68 (compound 2)<br>Group 2: 3 mice injected with NODAGA-LINKER-FOLATE-Ga68 (compound 2) |
| Time point | 1 h post-injection |

| Ratio | GROUP 1:<br>Alimta/NODAGA-LINKER-FOLATE-Ga68 | GROUP 2:<br>NODAGA-LINKER-FOLATE-Ga68 |
|---|---|---|
| tumor:kidney | 0.69 | 0.17 |
| tumor:liver | 10.49 | 6.64 |
| tumor:pancreas | 9.30 | 6.89 |
| tumor:blood | 49.33 | 64.85 |
| tumor:muscle | 13.32 | 9.95 |
| tumor:bone | 20.96 | 28.11 |
| tumor:parotid | 2.63 | 1.72 |

TABLE 2

Results with NODAGA-LINKER-FOLATE-Ga67 (compound 2' complexed by Ga67)

| | |
|---|---|
| Radioligand | NODAGA-LINKER-FOLATE-Ga67 (compound 2' complexed by Gallium 67) |
| Animals | Female nude mice (15-19 gr) under folate-free diet, bearing KB-tumors |
| Injection amount | 0.37 MBq/0.4 nmol/100 µl/mouse |
| Receptor blocking | Folic acid (100-fold excess), 5 min pre-injection |

TABLE 2-continued

Results with NODAGA-LINKER-FOLATE-Ga67 (compound 2' complexed by Ga67)

| Kidney blocking | Alimta 400 μg/100 μl/mouse, 1 h pre-injection |
|---|---|
| Groups: | 3 groups (3 mice/group) injected with NODAGA-LINKER-FOLATE-Ga67 |
| | 1 group (3 mice) injected with Folic acid 5 min before injection with NODAGA-LINKER-FOLATE-Ga67 (compound 2) |
| | 1 group (3 mice) injected with Alimta 1 h before injection with NODAGA-LINKER-FOLATE-Ga67 (compound 2) |
| Time point | 2 h, 4 h, 4 h blocking (with folic acid), 4 h (alimta), 24 h |

| Organs | 2 h | 4 h blocking with Folic acid | 4 h | 4 h Alimta pre-injection | 24 h |
|---|---|---|---|---|---|
| blood | 0.09 ± 0.02 | 0.00 ± 0.00 | 0.06 ± 0.01 | 0.04 ± 0.01 | 0.04 ± 0.02 |
| liver | 1.38 ± 0.50 | 0.06 ± 0.00 | 1.07 ± 0.18 | 0.88 ± 0.26 | 0.87 ± 0.16 |
| spleen | 0.48 ± 0.11 | 0.04 ± 0.01 | 0.46 ± 0.10 | 0.31 ± 0.13 | 0.37 ± 0.13 |
| lung | 1.32 ± 0.15 | 0.06 ± 0.00 | 1.36 ± 0.37 | 0.68 ± 0.18 | 0.94 ± 0.31 |
| kidney | 142.14 ± 15.46 | 6.49 ± 1.03 | 130.31 ± 14.65 | 19.13 ± 6.66 | 97.62 ± 11.59 |
| stomach | 1.58 ± 0.12 | 0.09 ± 0.06 | 1.47 ± 0.08 | 0.84 ± 0.31 | 1.01 ± 0.10 |
| intestine | 0.50 ± 0.12 | 0.08 ± 0.07 | 0.43 ± 0.16 | 0.50 ± 0.37 | 0.37 ± 0.13 |
| adrenal | 3.09 ± 0.52 | 0.02 ± 0.01 | 2.80 ± 0.10 | 1.75 ± 0.23 | 5.04 ± 5.96 |
| pancreas | 2.91 ± 0.08 | 0.05 ± 0.00 | 2.92 ± 0.11 | 2.20 ± 0.69 | 2.37 ± 0.17 |
| pituitary | 0.53 ± 0.24 | −0.02 ± 0.01 | 0.79 ± 0.74 | 0.59 ± 0.41 | 0.41 ± 0.39 |
| muscle | 1.49 ± 0.18 | 0.03 ± 0.00 | 2.12 ± 0.31 | 1.26 ± 0.38 | 1.14 ± 0.01 |
| Tumor KB | 18.42 ± 0.74 | 2.22 ± 0.12 | 16.29 ± 4.46 | 14.55 ± 5.54 | 14.32 ± 5.80 |
| Parotid gland | 9.10 ± 3.39 | 0.18 ± 0.06 | 8.58 ± 2.33 | 6.10 ± 2.09 | 5.57 ± 0.82 |

EXAMPLE 8

Imaging of NODAGA-LINKER-FOLATE-Ga 68 PET Imaging in Mice Model Bearing OVCAR-3 Tumor Similar protocol was used for OVCAR-3 tumor models.

For the kidney blocking the antifolate Alimta, at a concentration of 4 mg/ml in PBS pH 7.4 was used.

Figure 2:
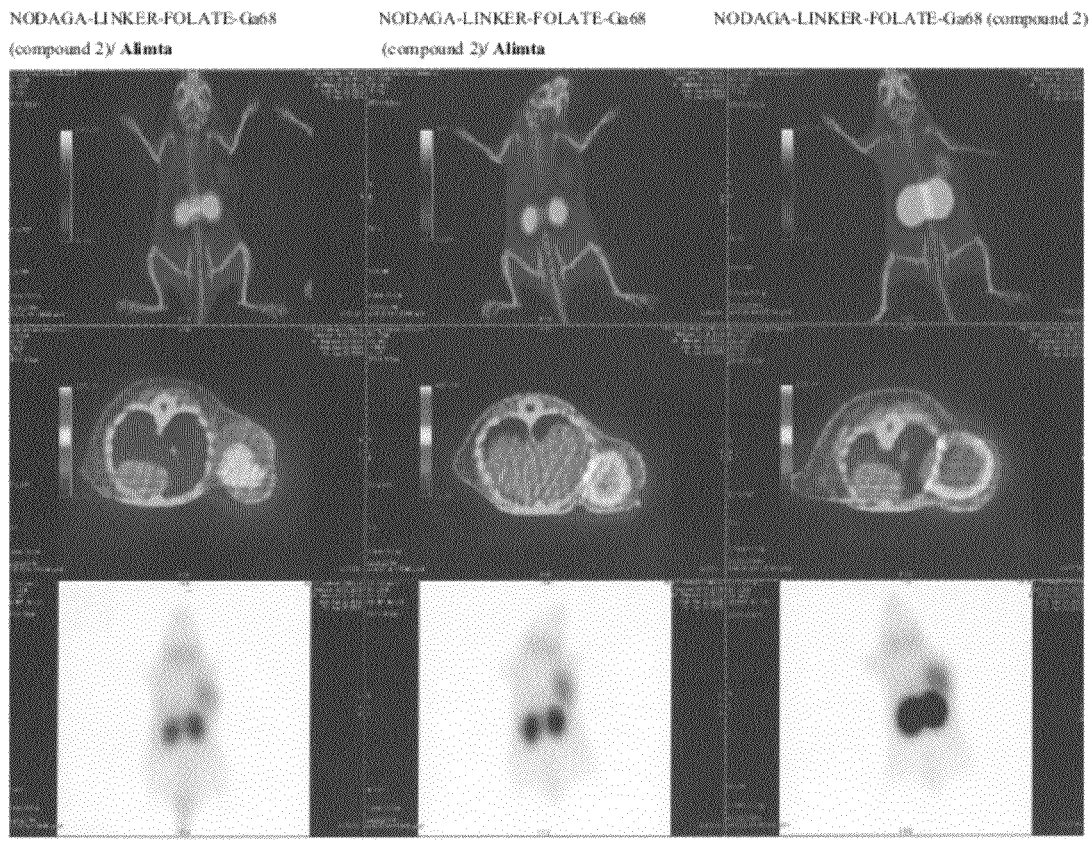
FIG. 2 depicts imaging of NODAGA-LINKER-FOLATE-Ga 68 with PET/CT in a tumor mouse model.

For the Folate Receptors blocking Folic acid in 100-fold excess (400 nmol/ml) in PBS pH 7.4 was used. For the in vivo evaluation the mice were grouped in 3 groups of 2-3 mice per group and injected. The biodistribution profile of the NODAGA-LINKER-FOLATE-Ga68 (example 2 compound 2) in the SCID mice bearing OVCAR-3 tumors is in agreement with those of example 7 (in KB tumor model). The PET/CT images (FIG. 2) showed clear visualization of the tumors, high uptake in the kidneys and negligible background, 1 h post injection of the radiotracer NODAGA-LINKER-FOLATE-Ga68.

Very satisfying PET/CT images are obtained in particular with compound 2:

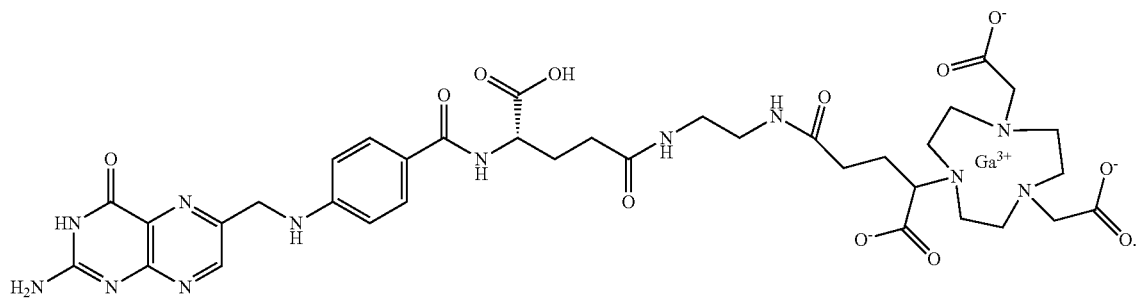

The invention claimed is:

1. A Ga68 complex of formula FOLATE-(LINKER)i-NOTA-Ga$^{68}$, wherein:
   FOLATE is a folate compound or a derivative thereof capable of targeting a folate receptor;
   NOTA is a chelate capable of complexing Ga68 having a NOTA scaffold or derivatives thereof;
   LINKER is a chemical group linking FOLATE and NOTA;
   i is an integer chosen between 0 and 1;

wherein
NOTA is formula (I):

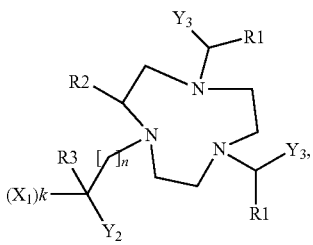

wherein
$Y_2$ is: —(C=O)—$Y_4$,

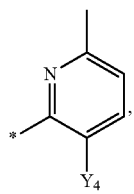

—$Y_4$ or NR4-CH$_2$—(C=O)—$Y_4$,
each of $Y_3$ is independently —(C=O)—$Y_4$ or

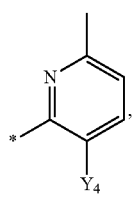

wherein
* is the binding site to NOTA;
$Y_4$ is —OH, or —NHR;
R is a $C_1$-$C_6$ alkyl group;
R4 is a hydrogen atom, a group —CH$_2$COOH and a benzyl group;
R1 is a hydrogen atom or a phenyl group substituted by the group NCS;
R2 is hydrogen, —(CH$_2$)j-COOH, —(CH$_2$)j-NH$_2$, —(CH$_2$)j-CO-$^Y$, or —(CH$_2$)j-NH$^Y$, in which j is an integer from 1 to 10, and Y is the binding site to LINKER when i=1, or to FOLATE when i=0;
n is an integer from 0 to 2;
k=0 or 1;
when i=1, $X_1$ is a group of formula —(CH$_2$)$_p$—$X_3$, wherein p is an integer of between 0 and 10, and $X_3$ is the binding site between NOTA and LINKER when i=1 and $X_3$ is selected from the group consisting of: —CONH—, —COO—, —NHCO—, —NH—, —CO— and —OCO—,
or
$X_1$ is a benzyl group substituted by an NO$_2$ group, a phenyl group substituted by a NCS or an OH group, or a group of formula:

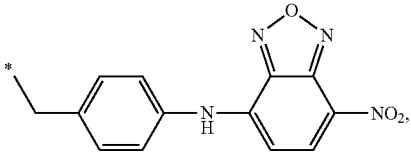 [SMILES: CCc1ccc(Nc2ccc([N+](=O)[O-])c3nonc23)cc1]

wherein * is the binding site to the NOTA,
or
when i=0, $X_1$ is FOLATE;
R3 is a hydrogen atom, a benzyl group substituted by an NO$_2$ group, a phenyl group substituted by an NCS or an OH group, a —(CH$_2$)$_2$—COOH group, or a group of formula:

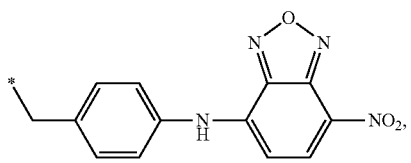 [SMILES: *Cc1ccc(Nc2ccc([N+](=O)[O-])c3nonc23)cc1]

wherein * is the binding site to NOTA
FOLATE is formula (A):

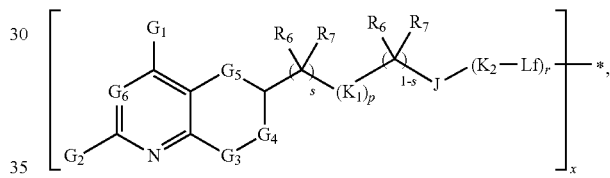

or (B):

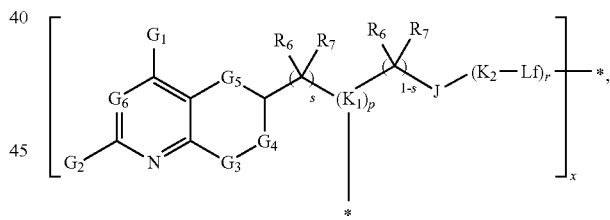

or tautomers thereof,
wherein
* is the site where FOLATE is bound to LINKER when i=1, or to NOTA when i=0;
a) $G_1$ is selected from the group consisting of: a halogen atom, R$_f$2, OR$_f$2, SR$_f$3 and NR$_f$4R$_f$5;
b) $G_2$ is selected from the group consisting of: a halogen atom, R$_f$2, OR$_f$2, SR$_f$3 and NR$_f$4R$_f$5;
c) $G_3$ is —(R$_f$6')C= or —N=, and $G_4$ is —(R$_f$6')C— or —N—, or
$G_3$ is —(R$_f$6')C— or —N—, and $G_4$ is —(R$_f$6')C= or —N=, or
$G_3$ and $G_4$ are each independently, —(R$_f$6')C(R$_f$7')— or —N(R$_f$4')—;
d) $G_5$ is absent or selected from the group consisting of: —(R$_f$6')C=, —N=, —(R$_f$6')C(R$_f$7')— and —N(R$_f$4')—;
e) J is a 5- or 6- membered aryl or heteroaryl group;

f) $G_6$ is N or C;

g) $K_1$ and $K_2$ are each selected independently from the group consisting of; —C($Z_f$)—, —C($Z_f$)O—, —OC($Z_f$)—, —N($R_f4''$)—, —C($Z_f$)—N($R_f4$), —N($R_f4''$)—C($Z_f$), —O—C($Z_f$)—N($R_f4''$)—, —N($R_f4''$)—C($Z_f$)—O—, N($R_f4''$)—C($Z_f$)—N($R_f5''$)—, —O—, —S—, —S(O)—, —S(O)$_2$—, —N($R_f4''$)S(O)$_2$—, —C($R_f6''$)($R_f7''$)—, —N(C≡CH)—, —N(CH$_2$—C≡CH)—, $C_1$-$C_{12}$ alkyl and $C_1$-$C_{12}$ alkoxy, wherein $Z_f$ is O or S;

h) $R_f2$, $R_f3$, $R_f4$, $R_f4'$, $R_f4''$, $R_f5$, $R_f5''$, $R_f6''$ and $R_f7''$ are each selected independently from the group consisting of: H, a halogen atom, $C_1$-$C_{12}$ alkyl, $C_1$-$C_{12}$ alkoxy, $C_1$-$C_{12}$ alkanoyl, $C_2$-$C_{12}$ alkenyl, $C_2$-$C_{12}$ alkynyl, ($C_1$-$C_{12}$ alkoxy)carbonyl, and ($C_1$-$C_{12}$ alkylamino) carbonyl;

i) $R_f6'$ and $R_f7'$ are each selected independently from the group consisting of: H, a halogen atom, $C_1$-$C_{12}$ alkyl and $C_1$-$C_{12}$ alkoxy, or $R_f6'$ and $R_f7'$ together form O═;

j) $R_6$ and $R_7$ are each independently H or $C_1$-$C_{12}$ alkyl;

k) $L_f$ is glutamine;

l) p, r and s are independently 0 or 1; and m) x is an integer of 1 to 5; and

LINKER is:

a single bond; or selected from the group consisting of:
—(CH$_2$)$_m$—, —(CH$_2$)$_m$CO—, —(CH$_2$)$_m$NHCO—, —(CH$_2$)$_m$CONH—, —(CH$_2$)$_m$CONH(CH$_2$)$_m$, —(CH$_2$)$_m$phenylNH—, —(CH$_2$)$_m$NH—, —NH(CH$_2$)$_m$NH—, —(CH$_2$)$_m$phenyl-, and —NH(CH$_2$)$_m$—, wherein m is an integer from 1 to 20;
(CH$_2$CH$_2$O)$_q$(CH$_2$)$_r$CO—, (CH$_2$CH$_2$O)$_q$(CH$_2$)$_r$NHCO—, —(CH$_2$CH$_2$O)$_q$(CH$_2$)r—, and (CH$_2$CH$_2$O)$_q$(CH$_2$)$_r$NH—, wherein q is an integer from 1 to 10, and r is an integer from 2 to 10;
—(CH$_2$)$_n$—CONH-PEG-,

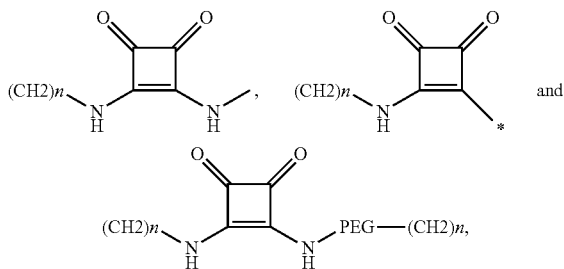

wherein * is the binding site to NOTA, and n is an integer from 1 to 5;
—CO—CH$_2$—O—(CH$_2$)$_r$—O—(CH$_2$)$_p$—O—CH$_2$—CO—, —CO—(CH$_2$)$_r$—CO$_2$—(CH$_2$)$_p$—OCO—(CH$_2$)$_s$—CO—, —CO—CH(OH)—CH(OH)—CO—, CO—(CH$_2$)$_r$—CO—, —CO—CH$_2$—O—(CH$_2$)$_r$—O—(CH$_2$)$_p$—O—CH$_2$—, —CO—(CH$_2$)$_r$—CO$_2$—(CH$_2$)$_p$—OCO—(CH$_2$)$_s$—, —CO—CH(OH)—CH(OH)— and —CO—(CH$_2$)$_r$—, wherein r is an integer from 1 to 20, p is an integer from 1 to 20, and s is an integer from 1 to 20;

—NH—(CH$_2$)$_t$—CO—, —NH—CH$_2$—(CH$_2$—O—CH$_2$)$_t$—CO— and —NH—CH$_2$—(CH$_2$—O—CH$_2$)$_t$-, wherein t is an integer from 1 to 10;

and

P1-l-P2, wherein P1 and P2 are independently selected from the group consisting of: O, S, NH, absent, CO$_2$, NHCO, CONH, NHCONH, NHCSNH, SO$_2$NH—, NHSO$_2$— and squarate, and wherein l is selected from the group consisting of: alkyl, alkoxyalkyl, polyalkoxyalkyl, polyethylene glycol, alkyl interrupted with one or more squarates or with one or more aryls, alkenyl, alkynyl, and alkyl interrupted with one or more groups selected from: —NH—, —O—, —CO—, —NH(CO)—, —(CO)NH—, —O(CO)—, and —(OC)O—, and wherein NOTA is complexed to Ga68.

2. The Ga68 complex of claim 1, wherein $G_1$ is NH$_2$ or OH, $G_2$ is NH$_2$, $G_3$ is —($R_f6'$)C═ or —N═, $G_4$ is —($R_f6'$)C— or —N—, $G_5$ is —($R_f6'$)C═ or —N═, J is a phenyl group, $G_6$ is N, $K_1$ is —N($R_f4''$)—, $K_2$ is —C($Z_f$)—, $Z_f$ is S or O and $L_f$ is glutamine.

3. The Ga68 complex of claim 2, wherein FOLATE is formula (a1) or (a2)

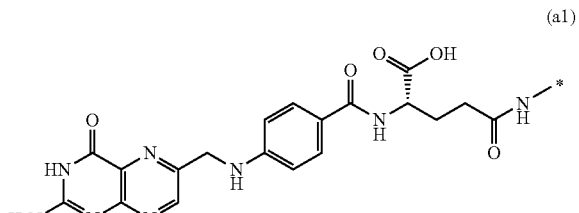

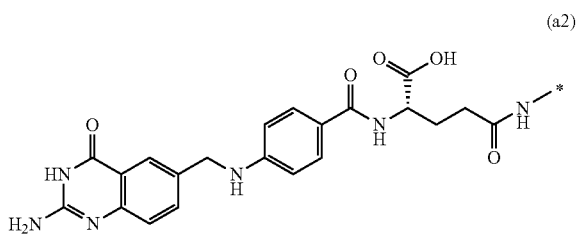

wherein * is the binding site to LINKER when i=1, or NOTA when i=0, and tautomers thereof.

4. The Ga68 complex of claim 1, wherein LINKER is —(CH$_2$)$_m$—, wherein m is an integer from 1 to 20.

5. The Ga68 complex of claim 1, having formula 1 or 2:

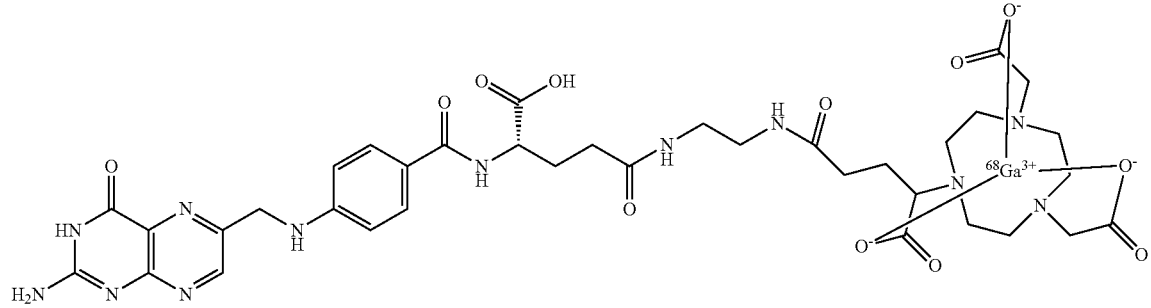

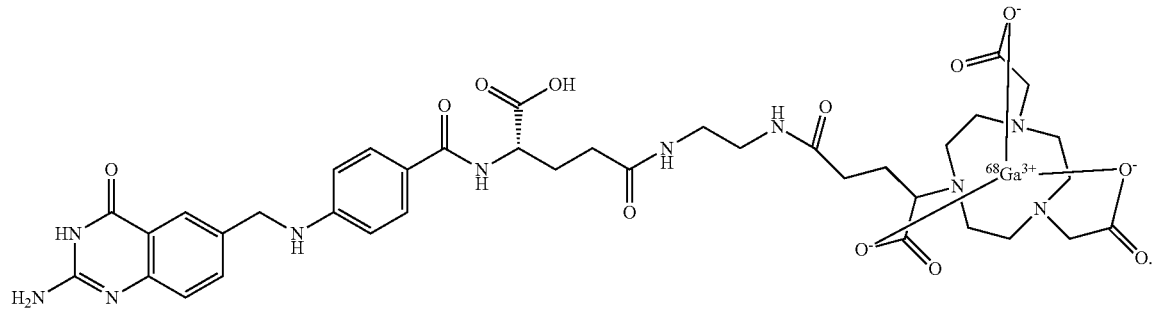

6. A composition comprising the Ga68 complex of claim 1 and a carrier agent.

7. A method of diagnosing ovarian cancer, which comprises:
   administering the composition of claim 6 to a patient in need thereof, and
   PET imaging said patient.

8. A method of monitoring the efficacy of a drug for treatment of ovarian cancer in a patient in need thereof, which comprises:
   a) administering the composition of claim 6 to said patient and PET imaging a region of the patient;
   b) administering said drug to said patient to treat ovarian cancer;
   c) repeating step a);
   d) comparing the image obtained in step a) to the image obtained in step c) to determine efficacy of said drug; and
   e) optionally adjusting the dosage and the timing of administration of said drug.

9. The Ga68 complex of claim 1, wherein R2 is hydrogen, —$(CH_2)j$-COOH, —$(CH_2)j$-$NH_2$, —$(CH_2)j$-CO—$^Y$ group, or —$(CH_2)j$-NH—$^Y$, and wherein j is 1.

* * * * *